United States Patent
Salem et al.

(10) Patent No.: US 9,572,894 B2
(45) Date of Patent: Feb. 21, 2017

(54) BIODEGRADABLE PARTICULATE FORMULATIONS

(75) Inventors: Aliasger K. Salem, Iowa City, IA (US); Sean M. Geary, Iowa City, IA (US); George J. Weiner, Iowa City, IA (US); Caitlin Lemke, Iowa City, IA (US); Yogita Krishnamachari, Iowa City, IA (US)

(73) Assignee: The University of Iowa Research Foundation, Iowa City, IA (US)

(*) Notice: Subject to any disclaimer, the term of this patent is extended or adjusted under 35 U.S.C. 154(b) by 392 days.

(21) Appl. No.: 13/878,561

(22) PCT Filed: Oct. 18, 2011

(86) PCT No.: PCT/US2011/056630
§ 371 (c)(1),
(2), (4) Date: Jan. 3, 2014

(87) PCT Pub. No.: WO2012/054425
PCT Pub. Date: Apr. 26, 2012

(65) Prior Publication Data
US 2014/0127253 A1    May 8, 2014

Related U.S. Application Data

(60) Provisional application No. 61/394,262, filed on Oct. 18, 2010, provisional application No. 61/394,254, filed on Oct. 18, 2010.

(51) Int. Cl.
| | |
|---|---|
| *A61K 47/48* | (2006.01) |
| *A61K 9/16* | (2006.01) |
| *A61K 31/704* | (2006.01) |
| *A61K 39/39* | (2006.01) |
| *A61K 39/00* | (2006.01) |

(52) U.S. Cl.
CPC ....... *A61K 47/48876* (2013.01); *A61K 9/1647* (2013.01); *A61K 31/704* (2013.01); *A61K 39/0011* (2013.01); *A61K 39/39* (2013.01); *A61K 47/48092* (2013.01); *A61K 2039/55511* (2013.01); *A61K 2039/55555* (2013.01); *A61K 2039/55561* (2013.01)

(58) Field of Classification Search
None
See application file for complete search history.

(56) References Cited

U.S. PATENT DOCUMENTS

| | | | | |
|---|---|---|---|---|
| 6,884,435 B1 * | 4/2005 | O'Hagan | ............ | A61K 9/1647 424/455 |
| 2004/0197312 A1 * | 10/2004 | Moskalenko | ........ | A61K 38/193 424/93.21 |
| 2007/0081972 A1 * | 4/2007 | Sandler | ................ | A61K 9/0024 424/85.1 |

FOREIGN PATENT DOCUMENTS

| | | | | |
|---|---|---|---|---|
| WO | WO 03/080111 | * | 10/2003 | ............ A61K 39/00 |
| WO | 2005030174 A1 | | 4/2005 | |
| WO | 2009088401 A2 | | 7/2009 | |
| WO | WO 2009/088401 | * | 7/2009 | ............ A61K 39/00 |
| WO | 2010050902 A1 | | 5/2010 | |
| WO | 2011026111 A1 | | 3/2011 | |

OTHER PUBLICATIONS

Coley WB, "The Treatment of Malignant Tumors by Repeated Inoculations of Erysipelas with a Report of Ten Original Cases," American Journal of Medical Sciences (1893); 105:487-511.
Brody JD, Ai WZ, Czerwinski DK, Torchia JA, Levy M, Advani RH, et al., "In situ vaccination with a TLR9 agonist induces systemic lymphoma regression: a phase I/II study," Journal of clinical oncology: official journal of the American Society of Clinical Oncology (2010); 28(28):4324-32. PMCID: 2954133.
Zappasodi R, Pupa SM, Ghedini GC, Bongarzone I, Magni M, Cabras AD, et al., "Improved clinical outcome in indolent B-cell lymphoma patients vaccinated with autologous tumor cells experiencing immunogenic death," Cancer research. (2010); 70(22):9062-72.
Obeid M, Panaretakis T, Joza N, Tufi R, Tesniere A, van Endert P, et al., "Calreticulin exposure is required for the immunogenicity of gamma-irradiation and UVC light-induced apoptosis," Cell death and differentiation (2007); 14 (10):1848-50.
Obeid M, Tesniere A, Ghiringhelli F, Fimia GM, Apetoh L, Perlettini JL, et al., "Calreticulin exposure dictates the immunogenicity of cancer cell death," Nature medicine (2007);13(1):54-61.
Ma Y, Aymeric L, Locher C, Mattarollo SR, Delahaye NF, Pereira P, et al., "Contribution of IL-17-producing {gamma} {delta} T cells to the efficacy of anticancer chemotherapy," The Journal of experimental medicine (2011);208 (3):491-503. PMCID: 3058575.
Salem AK, Weiner GJ., "CpG oligonucleotides as immunotherapeutic adjuvants: innovative applications and delivery strategies," Advanced drug delivery reviews (2009);61(3):193-4.
Weiner GJ, "CpG oligodeoxynucleotide-based therapy of lymphoid malignancies," Advanced drug delivery reviews (2009);61(3):263-7.
Lu JM, Wang X, Marin-Muller C, Wang H, Lin PH, Yao Q, et al., "Current advances in research and clinical applications of PLGA-based nanotechnology," Expert Rev Mol Diagn. (2009);9(4):325-41. PMCID: 2701163.
Zhang XQ, Dahle CE, Baman NK, Rich N, Weiner GJ, Salem AK, "Potent antigen-specific immune responses stimulated by codelivery of CpG ODN and antigens in degradable microparticles," J Immunother. (2007);30(5):469-78.
Zhang XQ, Dahle CE, Weiner GJ, Salem AK, "A comparative study of the antigen-specific immune response induced by co-delivery of (Continued)

*Primary Examiner* — Brad Duffy
*Assistant Examiner* — Nelson B Moseley, II
(74) *Attorney, Agent, or Firm* — Klintworth & Rozenblat IP LLC

(57) ABSTRACT

The present invention provides three-component compositions comprising microparticles, a tumor antigen, a first immune adjuvant, and a second immune adjuvant. Also provided are chemo-immunotherapeutic compositions comprising microparticles, a chemotherapeutic agent, and an immune adjuvant.

5 Claims, 11 Drawing Sheets

(56) References Cited

OTHER PUBLICATIONS

CpG ODN and antigen using fusion molecules or biodegradable microparticles," J. Pharm. Sci. (2007);96(12):3283-92.
Weinberg BD, Ai H, Blanco E, Anderson JM, Gao J., "Antitumor efficacy and local distribution of doxorubicin via intratumoral delivery from polymer millirods," J Biomed Mater Res A. (2007);81(1):161-70.
Idani H, Matsuoka J, Yasuda T, Kobayashi K, Tanaka N., "Intratumoral injection of doxorubicin (adriamycin) encapsulated in liposome inhibits tumor growth, prolongs survival time and is not associated with local or systemic side effects," Int. J. Cancer (2000);88(4):645-51.
Voulgaris S, Partheni M, Karamouzis M, Dimopoulos P, Papadakis N, Kalofonos HP., "Intratumoral doxorubicin in patients with malignant brain gliomas," Am. J. Clin. Oncol. (2002);25(1):60-4.
Li J, Song W, Czerwinski DK, Varghese B, Uematsu S, Akira S, et al., "Lymphoma immunotherapy with CpG oligodeoxynucleotides requires TLR9 either in the host or in the tumor itself," J. Immunol. (2007);179(4):2493-500.
Hartmann G, Weiner GJ, Krieg AM, "CpG DNA: a potent signal for growth, activation, and maturation of human dendritic cells," Proc. Natl. Acad. Sci., USA (1999);96(16):9305-10.
Weiner GJ, Liu HM, Wooldridge JE, Dahle CE, Krieg AM, "Immunostimulatory Oligodeoxynucleotides Containing the CpG Motif are Effective As Immune Adjuvants in Tumor Antigen Immunization," Proc. Natl. Acad. Sci., USA (1997);94 (20):10833-7.
Jahrsdorfer B, Hartmann G, Racila E, Jackson W, Muhlenhoff L, Meinhardt G, et al., "CpG DNA increases primary malignant B cell expression of costimulatory molecules and target antigens," J Leukoc Biol. (2001);69(1):81-8.
Jahrsdorfer B, Muhlenhoff L, Blackwell SE, Wagner M, Poeck H, Hartmann E, et al., "B-cell lymphomas differ in their responsiveness to CpG oligodeoxynucleotides," Clin Cancer Res. (2005);11(4):1490-9.
Link BK, Ballas ZK, Weisdorf D, Wooldridge JE, Bossier AD, Shannon M, et al., "Oligodeoxynucleotide CpG 7909 delivered as intravenous infusion demonstrates immunologic modulation in patients with previously treated non-Hodgkin lymphoma," J Immunother. (2006);29(5):558-68.
Leonard JP, Link BK, Emmanouilides C, Gregory SA, Weisdorf D, Andrey J, et al., "Phase I Trial of Toll-Like Receptor 9 Agonist PF-3512676 with and Following Rituximab in Patients with Recurrent Indolent and Aggressive Non-Hodgkin's Lymphoma," Clin Cancer Res. (2007);13(20):6168-74.
Zent CS, Smith BJ, Ballas ZK, Wooldridge JE, Link BK, Call TG, et al., "A Phase I Clinical Trial of CpG Oligonucleotide 7909 (PF-03512676) in Patients with Previously Treated Chronic Lymphocytic Leukemia," Leukemia & lymphoma (2012), 53:211-217.
Heckelsmiller K, Rall K, Beck S, Schlamp A, Seiderer J, Jahrsdorfer B, et al, "Peritumoral CpG DNA elicits a coordinated response of CD8 T cells and innate effectors to cure established tumors in a murine colon carcinoma model," J Immunol. (2002);169(7):3892-9.
Betting DJ, Yamada RE, Kafi K, Said J, van Rooijen N, Timmerman JM, "Intratumoral but not systemic delivery of CpG oligodeoxynucleotide augments the efficacy of anti-CD20 monoclonal antibody therapy against B cell lymphoma," J. Immunother.. (2009);32(6):622-31.
Molenkamp BG, van Leeuwen PAM, Meijer S, Sluijter BJR, Wijnands PGTB, Baars A, et al., "Intradermal CpG-B activates both plasmacytoid and myeloid dendritic cells in the sentinel lymph node of melanoma patients," Clin. Cancer Res. (2007);13(10):2961-9.
Topalian SL, Weiner GJ, Pardoll DM, "Cancer Immunotherapy Comes of Age," J. Clin. Oncol.. (2011) 29:4828-36.
Zou W, Chen L., "Inhibitory B7-family molecules in the tumour microenvironment," Nature Rev. Immunol. (2008);8 (6):467-77.
Hodi FS, O'Day SJ, McDermott DF, Weber RW, Sosman JA, Haanen JB, et al., "Improved survival with ipilimumab in patients with metastatic melanoma," N. Engl. J. Med. (2010);363(8):711-23.
Keir ME, Butte MJ, Freeman GJ, Sharpe AH., "PD-1 and its ligands in tolerance and immunity," Annu. Rev. Immunol. (2008);26:677-704.
Yang ZZ, Novak AJ, Ziesmer SC, Witzig TE, Ansell SM, "Attenuation of CD8(+) T-cell function by CD4(+)CD25(+) regulatory T cells in B-cell non-Hodgkin's lymphoma, " Cancer Res. (2006);66(20):10145-52. PMCID: 2680600.
Yang ZZ, Novak AJ, Stenson MJ, Witzig TE, Ansell SM, "Intratumoral CD4+CD25+ regulatory T-cell-mediated suppression of infiltrating CD4+ T cells in B-cell non-Hodgkin lymphoma," Blood (2006);107(9):3639-46. PMCID: 1895773.
Wilcox RA, Feldman AL, Wada DA, Yang ZZ, Comfere NI, Dong H, et al., "B7-H1 (Pd-L1, CD274) suppresses host immunity in T-cell lymphoproliferative disorders," Blood (2009);114(10):2149-58. PMCID: 2744574.
Houot R, Levy R., "T-cell modulation combined with intratumoral CpG cures lymphoma in a mouse model without the need for chemotherapy," Blood (2009);113(15):3546-52. PMCID: 2668854.
Weisman HF, Bartow T, Leppo MK, Marsh HC, Jr., Carson GR, Concino MF, et al., "Soluble human complement receptor type 1: in vivo inhibitor of complement suppressing post-ischemic myocardial inflammation and necrosis," Science (1990);249(4965):146-51.
Krishnamachari, Y., Salem, AK., "PLGA microparticles that co-deliver antigen and toll like receptor ligand adjuvants for applications in cancer immunotherapy," Abstract presented at 2009 AAPS Annual Meeting and Exposition (held Nov. 7, 2009-Nov. 12, 2009).
Krishnamachari, Y., Salem, AK. "Innovative strategies for co-delivering antigens and CpG oligonucleotides," Adv. Drug Deliv. Rev. (2009),61(3):205-17.
Krishnamachari, Y., Geary, SM, Lemke, CD, Salem, AK., "Nanoparticle Delivery Systems in Cancer Vaccines," Pharm. Res. (2010);28(2):215-36.
Haining, WN et al., "pH-triggered microparticles for peptide vaccination," J.. Immunol. (2004);173(4):2578-85.
Salem, Aliasger K., "Biodegradable microparticle delivery of antigens and adjuvants stimulate potent anti-tumor antigen-specific immune responses," Abstract BIOT-436 presented at The 232nd ACS National Meeting, San Francisco, CA (Sep. 10-14, 2006).
Singh, M. et al., "Nanoparticles and microparticles as vaccine-delivery systems," Expert Rev. Vaccines, (2007);6 (5):797-808.
Krishnamachari, Y, Salem, A, "PLGA microparticles based vaccines carriers for tumor immunotherapy," AAPS Journal (2010);12(S2).
International Search Report and Written Opinion dated Jul. 25, 2012 for PCT/US2011/056630, 17 pages.

* cited by examiner

BIODEGRADABLE PARTICULATE FORMULATIONS

CROSS REFERENCES TO RELATED APPLICATIONS

The present application is the National Stage of International Application No. PCT/US2011/056630, filed Oct. 18, 2011, which claims the benefit of U.S. Provisional Patent Application No. 61/394,254 filed Oct. 18, 2010 and U.S. Provisional Patent Application No. 61/394,262 filed Oct. 18, 2010. The content of these U.S. Provisional Patent Applications are hereby incorporated by reference in their entireties.

STATEMENT OF GOVERNMENT SUPPORT

This invention was made with government support under Grant No. 1R21CA13345-01 and 1R21CA128414-01-A2 awarded by the National Institutes of Health. The Government has certain rights in the invention.

INTRODUCTION

Cancer is still a major cause of death despite many decades of steady advancements in cancer therapies. Globally, approximately 12 million new cases of cancer are diagnosed every year and 6 million deaths are reported annually due to this disease. Currently applied and well established treatments for cancer include chemotherapy, radiotherapy and surgery. These treatments have proven to be variably effective depending on the type of cancer, the stage at which the cancer has been diagnosed and the anatomical location of the tumor. Chemotherapy has two major drawbacks in that: (1) it indiscriminately targets proliferating cells, thus resulting in killing of both tumor and healthy cells, and (2) multi-drug resistance can often ensue resulting in aggressive recurrence of the malignant disease. In addition, the therapeutic potential of chemotherapeutic agents such as doxorubicin has often been restricted by the immunosuppressive effect they can generate. The major limitation of radiotherapy and surgery is that these procedures fail to combat a metastasized tumor. Therefore, immunotherapy involving manipulating the patient's own immune system to recognize and destroy tumor cells with minimum detriment to healthy cells is being pursued as a safer and more efficacious approach to tumor therapy.

Cancer immunotherapy ideally involves: (1) specific attack upon the unwanted cancer cells with very limited non-specific killing, (2) the immune arsenal being systemic, therefore attacking any micrometastases and (3) possessing memory capable of fending off a relapse or recurrence of the same malignancy. Hence, one of the objectives of the novel therapeutic approaches of the invention is that chemotherapy may augment anti-tumor immunity and synergise with immunotherapies in vivo.

Lymphoma is particularly well suited for evaluation of immunization strategies. Lymphomas are known to be relatively immune-sensitive and respond to immunotherapy such as anti-lymphoma antibodies and cytokines. Lymphomas are often infiltrated with significant numbers of benign lymphocytes, as well as harmful or helpful monocytes and myeloid cells. B cell lymphoma cells can serve as antigen presenting cells (APCs). Involved nodes are often readily accessible for injection and for biopsy. Finally, evidence has been found suggesting that cancer vaccines, and in situ immunization, can be effective in treating lymphoma (2). Successful development of such a strategy would clearly be of great significance as a widely applicable new approach to lymphoma therapy.

Successful immunization by any avenue is believed to require effective presentation of tumor antigen. One approach to achieving this goal is use of dendritic cells loaded with apoptotic and necrotic autologous lymphoma cells. In a study using this approach, higher display of calreticulin by the lymphoma cells correlated with clinical response (3). Indeed, there is growing evidence that calreticulin exposure is required for optimal immunogenicity of tumor cells undergoing apoptosis (4, 5).

Typically, immunotherapy involves vaccination with tumor associate antigens (TAA) as potential targets of the immune system. Vaccines based on antigen alone, however, lack the ability to optimally activate the antigen presenting cells (APCs), including dendritic cells (DCs), to generate a significantly greater antigen-specific T-cell response. Additionally, a state of immune tolerance may also emerge. A typical strategy to overcome this limitation has been the use of immune adjuvants in order to improve the immunogenicity of the vaccines. A newer class of adjuvants known as toll-like receptor (TLR) ligands are believed to bind TLRs and thus elicit a $T_H$-1 polarized response. A TLR ligand can be classified accordingly to the class of TLRs it binds to, and the various TLRs can be roughly sub-classified according to the pathogen-associated molecular patterns (PAMPs) they recognize. TLR1, TLR2 and TLR6 are believed to detect lipopeptides, while TLR3, TLR7, TLR8 and TLR9 are thought to recognize nucleic acids. TLR5 is believed to detect flagellin, while TLR4 recognizes a diverse collection of lipopolysaccharides (LPS).

However, upon dual presentation by an antigen and a TLR ligand functioning as an adjuvant, a strong cytotoxic T-cell response is elicited that leads to apoptosis of tumor cells. There is increasing evidence that TLR ligands play an important role in bridging the gap between an innate and adaptive immune response. TLR signaling induces the production of pro-inflammatory cytokines and chemokines along with maturation of DCs. These mediators then induce a $T_H$-1 driven pathway activating cytotoxic T-lymphocytes (CTLs) and natural killer cells (NKs) promoting adaptive immunity.

CpG oligodeoxynucleotides (also known as "CpG ODN" or "CpG"), an important family of TLR ligands, are short single-stranded synthetic DNA molecules that contain a cytosine ("C") followed by a guanine ("G"). The "p" refers to the phosphodiester backbone of DNA, however some ODN have a modified phosphorothioate (PS) backbone. When these CpG motifs are unmethylated, they act as immunostimulants. CpG motifs are considered pathogen-associated molecular patterns (PAMPs) due to their abundance in microbial genomes but their rarity in vertebrate genomes. The CpG PAMP is recognized by the pattern recognition receptor (PRR) Toll-Like Receptor 9 (TLR9), which is constitutively expressed only in B cells and plasmacytoid dendritic cells (pDCs) in humans and other higher primates.

CpG ODN have been shown to have effect on human APCs (16), as immune adjuvants for cancer vaccines (17) and on B cell malignancies (18, 19). Further studies included evaluation in lymphoma of single agent CpG ODN (20), the combination of CpG ODN plus rituximab (21), and the combination CpG ODN plus radioimmunotherapy. Most recently, a two arm phase I/II trial of CpG ODN comparing the effects of a single dose of intravenous (i.v.) as opposed to subcutaneous (s.q.) CpG ODN in CLL (22) was conducted. Immunologic responses to CpG ODN included both direct effects on TLR9-expressing cells, and indirect effects resulting from production of cytokines produced by TLR9-expressing cells. Together, these studies show CpG ODN can lead to activation-induced cell death of malignant B cells and upregulation of CD40, CD80, CD86 and class II, thereby enhancing the ability of such cells to activate T cells. The direct and indirect effects of CpG ODN include activation of dendritic cells, NK cells and T cells.

DCs have shown distinct response pattern in terms of maturation, cytokine production and the level of immune response to each of these individual TLR-ligands. One study showed that Poly (I:C), a TLR-3 ligand, was found to be the most effective maturation stimulus for DC's. Additionally, activation of TLR-3 is believed to be an essential component to generate a NK cell response to a viral infection. Furthermore, several studies have shown that CpG ODN is likely to have the most potential for enhancing a CD8+ cell mediated immune response which is critical for anti-tumor activity. Recent studies by Gillanders et al. have shown that naïve CD8 cells have detectable levels of TLR-3 gene and hence treatment with a TLR-3 ligand such as Poly (I:C) could result in an enhanced antigen-specific cytotoxic activity by a direct ligation mechanism. While there are previous studies for co-delivery of an antigen and CpG, the number of studies for the co-delivery of an antigen and Poly (I:C) are however few.

Moreover, the fact that the distribution of these TLR receptors is highly species-dependent is a cause for concern. Whereas TLR-9 receptors in myeloid dendritic cells (mDCs) are ubiquitous in mouse-models, they are present to a slightly smaller extent in humans. In contrast, TLR-3 receptors are present in abundance in humans. Although TLR ligands individually may be ignored at certain low doses, no efforts have been made so far to explore the possibility that a host may have evolved to recognize a number of ligands when administered together, as a combined assault, and possibly mount immune responses against these combinations in a synergistic manner. If this hypothesis is correct, such a strategy would allow the immune system to rapidly respond to infection. However, such a possibility has not been explicitly explored so far.

Intravenous anthracyclines including doxorubicin ("dox") are used extensively and successfully to treat lymphoma. They are also known to trigger a process that has been described as "immunogenic cell death" that includes inducing expression of calreticulin by the treated cells. Such anthracycline-treated tumor cells can elicit activation of tumor-specific, interferon-γ-producing CD8+ T lymphocytes in the tumor bed (6).

Intratumoral (i.t.) injection of doxorubicin has resulted in local regression with limited toxicity in a number of models, including injection of PLGA microrods containing doxorubicin into rabbit liver tumors (12), doxorubicin-containing liposomes into murine fibrosarcoma (13) and a clinical trial of soluble doxorubicin directly into gliomas (14). In the glioma trial, ten daily injections led to local regression in six of the ten subjects and reported toxicity was limited to headache. However, none of these studies explored whether local doxorubicin treatment impacted on development of an active anti-tumor immune response.

SUMMARY OF THE INVENTION

Figure 1:
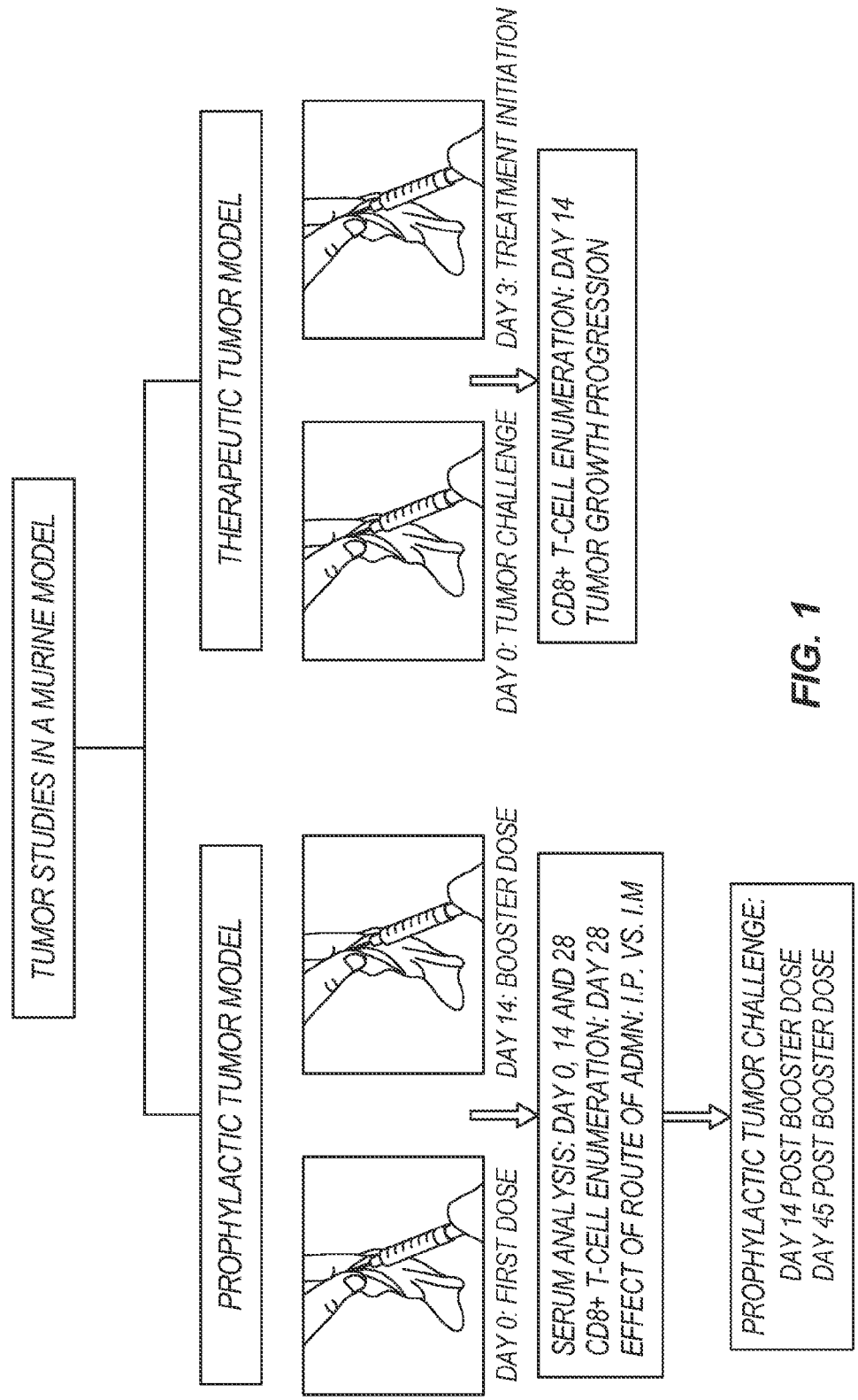
FIG. 1 illustrates a scheme of in vivo tumor studies in a murine model.

In a first aspect, the present invention provides three-component compositions for the therapy of tumors, comprising microparticles, an antigen and at least a first and second adjuvant.

In a second aspect, the present application provides methods for manufacturing three-component compositions comprising microparticles, an antigen, and at least two adjuvants.

In a third aspect, the present invention provides chemo-immunotherapeutic compositions comprising microparticles, a chemotherapeutic agent, and an immune adjuvant.

In a fourth aspect, the present invention provides methods for manufacturing chemo-immunotherapeutic compositions comprising microparticles, a chemotherapeutic agent, and an immune adjuvant.

In a fifth aspect, the present invention provides methods for the treatment of cancer based on the administration of a therapeutic amount of the three-component compositions of the first aspect of the invention.

In a sixth aspect, the present invention provides methods for the treatment of cancer based on the administration of a therapeutic amount of the chemo-immunotherapeutic compositions of the third aspect of the invention.

DEFINITIONS

A polymer precursor is a compound that will form a polymer, for example when it comes into contact with a polymerization activator suitable to the polymer precursor. Classes of polymer precursors include polyester precursors such as lactic acid, glycolic acid, lactide and glycolide, and prepolymers such as oligomers still capable of further polymerization.

A compound is a molecule that contains at most 100 repeating units. This is in contrast to a polymer, which contains more than 100 repeating units.

A polymeric material is a material comprising one or more polymers.

A monomer, or monomeric unit, is a repeating unit in a polymer. A monomer may be labeled according to the polymer precursor it is derived from. For example, a "glycolic acid" monomer is commonly meant as a monomer derived from glycolic acid or its cyclic 1,4-dioxane-2,5-dione dimer known as glycolide. Similarly, a "lactic acid" monomer is commonly meant as a monomer derived from lactic acid or its cyclic 1,4-dioxane-2,5-dione dimer known as lactide.

PLGA or poly(lactic-co-glycolic acid) is a copolymer commonly synthesized by means of ring-opening co-polymerization of glycolide and lactide. During the co-polymerization reaction, successive monomeric units (of glycolic or lactic acid) are linked together in PLGA by ester linkages, thus yielding an aliphatic polyester as a product. Depending on the ratio of lactide to glycolide used for the polymerization, different forms of PLGA can be obtained: these are usually identified in regard to the precursors' molar ratio used (e.g. PLGA 75:25 identifies a copolymer whose composition is 75% lactic acid and 25% glycolic acid, and PLGA 85:15 identifies a copolymer whose composition is 85% lactic acid and 15% glycolic acid).

When introducing elements of aspects of the invention or the embodiments thereof, the articles "a," "an," "the," and "said" are intended to mean that there are one or more of the elements. The terms "comprising," "including," and "having" are intended to be inclusive and mean that there may be additional elements other than the listed elements. The word "or" means any one member of a particular list and also includes any combination of members of that list, unless otherwise specified.

The term "about" is used herein to mean approximately, roughly, around, or in the region of. When the term "about" is used in conjunction with a numerical range, it modifies that range by extending the boundaries above and below the numerical values set forth. Unless otherwise stated, the term "about" is used herein to modify a numerical value above and below the stated value by a variance of 20 percent up or down (higher or lower).

The term "polynucleotide" as used herein refers to a naturally occurring or synthetic polynucleotide, whether DNA or RNA or DNA-RNA hybrid, single-stranded or double-stranded, sense or antisense, which is capable of hybridization to a complementary nucleic acid by Watson-Crick base-pairing. Polynucleotides can also include nucleotide analogs (e.g., BrdU), and non-phosphodiester internucleoside linkages (e.g., peptide nucleic acid (PNA) or thiodiester linkages). In particular, polynucleotides can include, without limitation, DNA, RNA, cDNA, gDNA, ssDNA or dsDNA or any combination thereof.

As used herein, "treatment" is an approach for obtaining beneficial or desired clinical results. For purposes of this invention, beneficial or desired clinical results include, but are not limited to, one or more of lessening severity, alleviation of one or more symptoms associated with cancer.

For the purposes of the present invention, an "effective amount" of drug, compound, or pharmaceutical composition is an amount sufficient to effect beneficial or desired clinical results in the treatment of cancer. An effective amount can be administered in one or more administrations. As is understood in the clinical context, an effective amount of a drug, compound, or pharmaceutical composition may or may not be achieved when administered in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

An "individual" is a vertebrate, preferably a mammal, more preferably a human. Mammals include, but are not limited to, farm animals (such as cows), sport animals, pets (such as cats, dogs and horses), primates, mice and rats.

As used herein, "pharmaceutically acceptable carrier" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%) saline. Compositions comprising such carriers are formulated by well known conventional methods (see, for example, Remington's Pharmaceutical Sciences, 18th edition, A. Gennaro, ed., Mack Publishing Co., Easton, Pa., 1990; and Remington, The Science and Practice of Pharmacy 20th Ed. Mack Publishing, 2000).

The term "antigen" is used herein to mean a substance that, when introduced into the body, triggers the production of an antibody by the immune system, which will then bind to the antigen that is recognized as a foreign and potentially harmful invader.

The term "adjuvant" is used herein to mean any substance that acts to accelerate, prolong, or enhance antigen-specific immune responses when used in combination with vaccine antigens.

The term "diameter" is used herein to mean the length of the longest straight segment connecting two points on the surface of a given object, wherein the entire length of the segment lies within said object.

The term "microparticle" is used herein to mean a particle between 10 nm and 100 µm in diameter.

DESCRIPTION OF THE INVENTION

A first aspect of the invention is based on the discovery that a combination of two or more adjuvants, when co-delivered in a cocktail with an antigen, will exhibit a synergistic anti-tumor effect and will generate a stronger immunostimulatory response in comparison to the delivery of the antigen alone. Without being bound to any particular theory, this is believed to be achieved by the increased production of desirable cytokines and chemokines to steer a strong $T_H$-1 polarized response for effective anti-tumor immunity.

While adjuvants such as TLR ligands exhibit potent immunostimulatory effects, they can be subject to rapid enzymatic degradation, impeding their effective delivery into the endosomal compartment. The present invention overcomes this problem by providing a microparticulate carrier to co-entrap the tumor associated antigen (TAA) of interest and either one or more adjuvants, for a co-delivery of a cocktail for the treatment of tumors. Delivery in the form of a microparticle ensures effective phagocytosis and also helps in providing a controlled delivery of therapeutic agents. The present invention thus provides a novel microparticulate carrier as a powerful prophylactic and therapeutic tool for the therapy of tumors, including solid tumors.

Accordingly, in this first aspect, the present invention provides "three-component" compositions for the therapy of tumors, comprising microparticles, an antigen and at least a first and second adjuvant. Without being bound to any particular theory, it is believed that microparticles serve as ideal carriers for the following reasons: (1) the ability of the microparticles to protect the antigen from rapid degradation and clearance; (2) favorable release profile where sustained release of the antigen occurs for lengthy periods (>30 days); and (3) the efficiency with which microparticles are taken up by DCs. Preferably, and especially when the antigen is susceptible to rapid degradation and clearance, the antigen and least one of the adjuvants are entrapped inside the microparticles. The other adjuvant may also be entrapped inside the microparticles, or, if preferable, adsorbed on their surface. To increase the amount of adsorbed adjuvant, the surface of the particles may be modified with an adsorption enhancer.

Preferably, the microparticles comprise at least one polymeric material. More preferably, the polymeric material is biodegradable. Preferred polymeric materials include: silk, elastin, chitin, chitosan, poly($\alpha$-hydroxy acids), poly(anhydrides), and poly(orthoesters). More particularly, example polymeric materials include polyethylene glycol, poly(lactic acid), poly(glycolic acid), copolymers of lactic and glycolic acid, copolymers of lactic and glycolic acid with polyethylene glycol, poly(E-caprolactone), poly(3-hydroxybutyrate), poly(p-dioxanone), polypropylene fumarate, poly(orthoesters), polyol/diketene acetals addition polymers, poly(sebacic anhydride) (PSA), poly(carboxybiscarboxyphenoxyphenoxy hexone (PCPP) poly[bis(p-carboxypheonoxy)methane] (PCPM), copolymers of SA, CPP and CPM, poly(amino acids), poly(pseudo amino acids), polyphosphazenes, derivatives of poly[(dichloro)phosphazenes] and poly[(organo)phosphazenes], poly-hydroxybutyric acid, or S-caproic acid, polylactide-co-glycolide, polylactic acid, and polyethylene glycol. Polyesters are particularly preferred. Most preferred is PLGA, especially PLGA 75:25 and PLGA 85:15.

The microparticles are preferably of dimensions suitable for strong uptake by cells. Average particle diameters are preferably from about 100 nm to about 20 µm. More preferably, average particle diameters are from about 200 nm to about 15 µm, and most preferably from about 500 nm to about 10 µm.

Example tumor associated antigens ("TAAs") can be obtained, for instance, from tumor cells, for example by entrapping tumor cell lysate in the microparticles. The lysate can be made from one or more cancer cells such as breast cancer cells, head and neck cancer cells, lung cancer cells, stomach cancer cells, esophageal cancer cells, skin cancer cells, colon cancer cells, ovarian cancer cells, prostate cancer cells, testicular cancer cells, uterine cancer cells, cervical cancer cells, pancreatic cancer cells, or liver cancer cells. A tumor cell lysate may comprise a partially purified portion of a lysate, that is one or more components of the lysate that have been isolated from other components of the lysate using methods know in the art. The cells may be taken, for example, from an individual who may suffer from recurrent cancer, metastatic cancer, or multi-drug resistant cancer. The particles may also be used to entrap a single tumor specific antigen that has been identified to be specific to a tumor cell type. For example, prostate specific antigen (PSA) is specific to prostate cancer while MARTI and tyrosine related protein 2 (TRP-2) are specific to melanoma.

If the surface of the microparticles is modified with an adsorption enhancer, the enhancer is preferably selected in order to increase the amount of adjuvant adsorbed. Accordingly, a cationic polymer is a preferred enhancer for the adsorption of negatively-charged TLR ligands such as CpG. Preferred cationic polymers include polyethylenimine (PEI), polyamidoamine (PAMAM), polylysine, and chitosan. Conversely, anionic polymers are preferred enhancers for the adsorption of positively-charged adjuvants. Preferred anionic polymers include alginate, polyglutamate, and sulfonated polymers. Neutral polymers, such as polyethylene glycol (PEG) and polypropylene glycol (PPG) are preferred for enhancing the adsorption of adjuvants bearing no electric charge or whose charge is insufficient to yield a significant adsorption enhancement by means of negatively- or positively-charged adsorption enhancers.

The first and second adjuvants are preferably chosen from among ligands of membrane-bound pattern recognition receptors, or PRRs. More preferred are TLR ligands, either synthetic or derived from natural sources such as bacteria, fungi, protozoa, and viruses. Example TLR ligands include $Pam_3CSK_4$, JBT3002, OspA, Mycoplasmal Macrophage-activating Lipopeptide-2 (MALP-2), Glycosylphosphatidylinositol (GPI), Polyinosine-polycytidylic Acid (poly(I:C)), Flavolipin, Acyclic Lipid A-like Analog, Type III Repeat Extra Domain A (EDA), LMW Oligosaccharides of Hyaluronic Acid (sHA), Polysaccharide Fragments of Heparan Sulfate Host, Fusion Protein of RSV, Envelope Proteins of MMTV, Glycoinositolphospholipids (GIPLs), Lipid A, Flagellin, Mycoplasmal Macrophage-activating Lipopeptide-2 (Malp-2), Diacylated Macrophage-activating Lipopeptide-2, Diacylated Lipopeptide FSL-1, Diacylated Lipopeptide $Pam_2CSK_4$, Soluble Tuberculosis Factor (STF), Heat Shock Proteins, Imiquimod, Gardiquimod, Resiquimod (R-848), S-27610, Loxoribine, TOG, 3M-13, 3M-2, Bropirimine, CpG ODNs, AT-ODNs, and Hemozoin. More preferably, the first adjuvant is a TLR-3 ligand, such as poly(I:C), and the second adjuvant is a TLR-9 ligand, such as a CpG.

In a second aspect, the present application provides methods for manufacturing three-component compositions comprising microparticles, an antigen, and at least two adjuvants. Preferably, the antigen and the adjuvants are entrapped within the microparticles. Alternatively, the antigen and one of the adjuvants are entrapped in the microparticles and the other adjuvant is adsorbed on the surface of the particles. To achieve this, the microparticles may be linked to an adsorption enhancer that increases the amount of adjuvant adsorption on their surface.

The particles may be produced by methods known in the art, such as spray drying, spontaneous emulsification solvent diffusion (SESD), double-emulsion solvent-evaporation, double-emulsion solvent-evaporation, modified solvent evaporation DNA-organic phase self-emulsification (DOPSM), emulsion-diffusion-evaporation, cryopreparation, and modified phase inversion/solvent diffusion. A preferred synthetic route involves the double emulsion solvent diffusion (DES-D) method. This method is based on forming a primary reaction mixture comprising a polymeric material, the antigen, a first adjuvant, water, a solvent immiscible with water, and a first emulsifier. Optionally, a second adjuvant may also be included in the primary reaction mixture. The primary reaction mixture is used to prepare a primary emulsion, and the primary emulsion is combined with a solution comprising water and a second emulsifier, where the second emulsifier may be the same as the first emulsifier, to form a secondary w/o/w (water/oil/water) emulsion. The water-immiscible solvent is removed from the secondary emulsion, for example by evaporation, yielding microparticles that may subjected to further processing steps, such as washing and lyophilization, as desired.

The polymeric material is preferably biodegradable. Preferred polymeric materials include: silk, elastin, chitin, chitosan, poly(α-hydroxy acids), poly(anhydrides), and poly(orthoesters). More preferred polymeric materials include polyethylene glycol, poly(lactic acid), poly(glycolic acid), copolymers of lactic and glycolic acid, copolymers of lactic and glycolic acid with polyethylene glycol, poly(E-caprolactone), poly(3-hydroxybutyrate), poly(p-dioxanone), polypropylene fumarate, poly(orthoesters), polyol/diketene acetals addition polymers, poly(sebacic anhydride) (PSA), poly(carboxybiscarboxyphenoxyphenoxy hexone (PCPP) poly[bis(p-carboxypheonoxy)methane] (PCPM), copolymers of SA, CPP and CPM, poly(amino acids), poly(pseudo amino acids), polyphosphazenes, derivatives of poly[(dichloro)phosphazenes] and poly[(organo) phosphazenes], poly-hydroxybutyric acid, or S-caproic acid, polylactide-co-glycolide, polylactic acid, and polyethylene glycol. Polyesters are particularly preferred. Most preferred is PLGA, especially PLGA 75:25 and PLGA 85:15.

The tumor associated antigen may be added to the first reaction mixture in the form of a tumor cell lysate. The lysate can be made from one or cancer cells such as breast cancer cells, head and neck cancer cells, lung cancer cells, stomach cancer cells, esophageal cancer cells, skin cancer cells, colon cancer cells, ovarian cancer cells, prostate cancer cells, testicular cancer cells, uterine cancer cells, cervical cancer cells, pancreatic cancer cells, or liver cancer cells. A tumor cell lysate may comprise a partially purified portion of a lysate, that is one or more components of the lysate that have been isolated from other components of the lysate using methods know in the art. The cells may be taken, for example, from an individual who may suffer from recurrent cancer, metastatic cancer, or multi-drug resistant cancer. The first reaction mixture may also be formed with a single tumor specific antigen such as prostate PSA, MARTI, or TRP-2.

The first and second adjuvants are preferably chosen from among ligands of membrane-bound pattern recognition receptors, or PRRs. More preferred are TLR ligands, either synthetic or derived from natural sources such as bacteria, fungi, protozoa, and viruses. Example TLR ligands include $Pam_3CSK_4$, JBT3002, OspA, Mycoplasmal Macrophage-activating Lipopeptide-2 (MALP-2), Glycosylphosphatidylinositol (GPI), Polyinosine-polycytidylic Acid (poly (I:C)), Flavolipin, Acyclic Lipid A-like Analog, Type III Repeat Extra Domain A (EDA), LMW Oligosaccharides of Hyaluronic Acid (sHA), Polysaccharide Fragments of Heparan Sulfate Host, Fusion Protein of RSV, Envelope Proteins of MMTV, Glycoinositolphospholipids (GIPLs), Lipid A, Flagellin, Mycoplasmal Macrophage-activating Lipopeptide-2 (Malp-2), Diacylated Macrophage-activating Lipopeptide-2, Diacylated Lipopeptide FSL-1, Diacylated Lipopeptide $Pam_2CSK_4$, Soluble Tuberculosis Factor (STF), Heat Shock Proteins, Imiquimod, Gardiquimod, Resiquimod (R-848), S-27610, Loxoribine, TOG, 3M-13, 3M-2, Bropirimine, CpG ODNs, AT-ODNs, and Hemozoin. More preferably, the first adjuvant is a TLR-3 ligand, such as poly(I:C), and the second adjuvant is a TLR-9 ligand, such as a CpG.

The water-immiscible solvent preferably comprises one or more organic solvents. Preferred organic solvents include those with low or no solubility in water, for instance alkyl solvents such as pentane and hexane, haloalkyls such as dichloromethane, trichloromethane, and tetrachloromethane, aryl such as benzene and toluene, and ether such as diethyl ether and methyl tert-butyl ether. Solvents may also be used which are miscible or partially miscible with water, for example alcohols such as methanol and ethanol, acetonitrile and acetone, provided that an emulsion can be formed from the first reaction mixture. As is well known in the art, solvents that are miscible with pure water can still yield two immiscible liquid phases in the presence of compounds such as salts, so the term "water-immiscible solvent" should not be restrictively read as a solvent not miscible with water under any circumstances, but rather as a solvent that, when mixed with the other ingredients of the first reaction mixture, gives rise to two immiscible liquid phases that can be formed into an emulsion.

The second adjuvant may be adsorbed to the microparticles instead of being included in the primary emulsion, for example in cases where retention of the second adjuvant by the microparticles is poor. As mentioned above, the particles may be modified with an adsorption enhancer in order to enhance adjuvant adsorption, for example by covalently bonding or adsorbing the enhancer to the particle surface. To this end, the enhancer may be conjugated to the microparticles by means of cross-linking reactions commonly used to attach new moieties to the functional groups of polymers, proteins, and other molecules. Among such functional groups, carboxyls (—COOH), primary amines (—$NH_2$), sulfihydryls (—SH), and carbonyls (—CHO) account for the vast majority of cross-linking reactions.

A number of chemically reactive cross-linking compounds, or cross-linkers have been characterized and used to target functional groups for cross-linking reactions. For example, when the surface of the microparticles features carboxyl groups and the adsorption enhancer has primary amine groups, or vice versa, a carbodiimide, such as 1-ethyl-3-(3-dimethylaminopropyl) carbodiimide) (EDC), N,N'Diisopropylcarbodiimide (DIC), or N,N'-Dicyclohexylcarbodiimide (DCC) may be used to facilitate the linking of said carboxyl groups with said primary amine groups, thereby forming amidic cross-linkages. N-hydroxysuccinimide (NHS) or its water-soluble analog (Sulfo-NHS) is often included in EDC coupling protocols to improve the efficiency of the amide group-forming reaction. Alternatively, the reaction may be facilitated by forming an imidoester of the carboxyl group and reacting it with primary amines.

More generally, crosslinkers are selected on the basis of their chemical reactivity and specificity for the functional groups present on the particle surface and enhancer together with other chemical properties that affect their behavior in different applications. In cases where the cross-linker becomes a part of the product of the cross-linking reaction, for instance by binding the particle at one end and the adsorption enhancer at the other, a cross-linker having an appropriate spacer arm length, i.e. the distance spanned by the cross-linker to connect the particle and enhancer, may be chosen to best suit the formulation at hand. A cross-linker with a cleavable arm may also be chosen, thus providing a linkage that can be broken when desired. Additionally, spacer arms of different hydrophobicity may be chosen to influence the water-solubility and cell membrane permeability of the particles.

As mentioned above, the choice of an enhancer will be largely dictated by the nature of the adjuvant to be adsorbed to the particle. Accordingly, a cationic polymer is a preferred enhancer for the adsorption of negatively-charged adjuvants such as CpG. Preferred cationic polymers include polyethylenimine (PEI), polyamidoamine (PAMAM), polylysine, and chitosan. Conversely, anionic polymers are preferred enhancers for the adsorption of positively-charged adjuvants. Preferred anionic polymers include alginate, polyglutamate, and sulfonated polymers. Neutral polymers, such as polyethylene glycol (PEG) and polypropylene glycol (PPG) are preferred for enhancing the adsorption of adjuvants bearing no electric charge or insufficient charge for increasing adsorption by means of negatively- or positively-charged adsorption enhancers.

In a third aspect, the present application provides novel "chemo-immunotherapeutic" compositions where the microparticle carrier system of the invention is used for the co-delivery of chemotherapeutic and immunotherapeutic agents. This aspect is based on the discovery that in situ delivery of chemotherapeutic agents that are known to induce immunogenic cell death, such as anthracyclins, impacts on the development of an active anti-tumor immune response. Without being bound to any particular theory, it is believed that in situ immunogenic cell death induced by chemotherapeutic agents causes the release of tumor antigen, enhances antigen presentation, and maintains the T cell response, all in the same microenvironment, and in a controlled fashion. In this third aspect, a microparticulate carrier is used to co-entrap a chemotherapeutic agent and an adjuvant for a co-delivery. A microparticulate-based approach ensures effective phagocytosis and also helps mitigate the toxic and immunosuppressive effects of chemotherapeutic agents by a reduction in the dose owing to co-delivery with the adjuvant and by providing a controlled delivery of both therapeutic agents.

Accordingly, in this third aspect, the present invention provides chemo-immunotherapeutic compositions comprising microparticles, a chemotherapeutic agent, and an immune adjuvant. The microparticulate carrier allows for an easier co-delivery of agents that are difficult to co-deliver in the same solution. For example, the anthracyclin chemotherapeutic agent doxorubicin is a weak base with a $pK_a$ of 8.3, thereby bearing a positive charge at a pH between 5 and 7, the typical pH of administration in physiological conditions. By contrast, the oligonucleotide CpG bears a negative charge in the same pH range. Accordingly, owing to the opposing charges and the high concentration that is required for therapeutic activity, it is not possible to co-deliver them together in the same solution. The microparticle-based carrier system of the invention can circumvent this problem and co-deliver both such agents without any mutual interference. In this novel formulation, it is believed that doxorubicin is entrapped inside the PLGA microparticle matrix and CpG is adsorbed electrostatically on the surface of the PLGA microparticle. Moreover, the adsorption of CpG may be increased by modifying the particles with a positively-charged adsorption enhancer such as PEI, PAMAM, polylysine, or chitosan.

Preferably, the microparticles comprise at least one polymeric material. More preferably, the polymeric material is biodegradable. Preferred polymeric materials include: silk, elastin, chitin, chitosan, poly(α-hydroxy acids), poly(anhydrides), and poly(orthoesters). More particularly, example polymeric materials include polyethylene glycol, poly(lactic acid), poly(glycolic acid), copolymers of lactic and glycolic acid, copolymers of lactic and glycolic acid with polyethylene glycol, poly(E-caprolactone), poly(3-hydroxybutyrate), poly(p-dioxanone), polypropylene fumarate, poly(orthoesters), polyol/diketene acetals addition polymers, poly(sebacic anhydride) (PSA), poly(carboxybiscarboxyphenoxyphenoxy hexone (PCPP) poly[bis(p-carboxypheonoxy) methane] (PCPM), copolymers of SA, CPP and CPM, poly(amino acids), poly(pseudo amino acids), polyphosphazenes, derivatives of poly[(dichloro)phosphazenes] and poly[(organo) phosphazenes], poly-hydroxybutyric acid, or S-caproic acid, polylactide-co-glycolide, polylactic acid, and polyethylene glycol. Polyesters are particularly preferred. Most preferred is PLGA, especially PLGA 75:25 and PLGA 85:15.

The microparticles are preferably of dimensions suitable for strong uptake by cells. Average particle diameters are preferably from about 100 nm to about 20 μm. More preferably, average particle diameters are from about 250 nm to about 15 μm, and most preferably from about 500 nm to about 10 μm.

If the surface of the microparticles is modified with an adsorption enhancer, the enhancer is preferably selected in order to increase the amount of adjuvant adsorbed. Accordingly, a cationic polymer is a preferred enhancer for the adsorption of negatively-charged TLR ligands such as CpG. Preferred cationic polymers include polyethylenimine (PEI), polyamidoamine (PAMAM), polylysine, and chitosan. Conversely, anionic polymers are preferred enhancers for the adsorption of positively-charged adjuvants. Preferred anionic polymers include alginate, polyglutamate, and sulfonated polymers. Neutral polymers, such as polyethylene glycol (PEG) and polypropylene glycol (PPG) are preferred for enhancing the adsorption of adjuvants bearing no electric charge or whose charge is insufficient for significantly adsorption by means of negatively- or positively-charged adsorption enhancers.

The adjuvant is preferably chosen from among ligands of membrane-bound pattern recognition receptors, or PRRs. More preferred are TLR ligands, either synthetic or derived from natural sources such as bacteria, fungi, protozoa, and viruses. Example TLR ligands include $Pam_3CSK_4$, JBT3002, OspA, Mycoplasmal Macrophage-activating Lipopeptide-2 (MALP-2), Glycosylphosphatidylinositol (GPI), Polyinosine-polycytidylic Acid (poly(I:C)), Flavolipin, Acyclic Lipid A-like Analog, Type III Repeat Extra Domain A (EDA), LMW Oligosaccharides of Hyaluronic Acid (sHA), Polysaccharide Fragments of Heparan Sulfate Host, Fusion Protein of RSV, Envelope Proteins of MMTV, Glycoinositolphospholipids (GIPLs), Lipid A, Flagellin, Mycoplasmal Macrophage-activating Lipopeptide-2 (Malp-2), Diacylated Macrophage-activating Lipopeptide-2, Diacylated Lipopeptide FSL-1, Diacylated Lipopeptide $Pam_2CSK_4$, Soluble Tuberculosis Factor (STF), Heat Shock Proteins, Imiquimod, Gardiquimod, Resiquimod (R-848), S-27610, Loxoribine, TOG, 3M-13, 3M-2, Bropirimine, CpG ODNs, AT-ODNs, and Hemozoin. More preferably, the adjuvant is a TLR-9 ligand, such as a CpG.

The chemotherapeutic agent may be any drug used in the treatment of cancer. Example drug families include, but are not limited to, anthracyclines, taxanes, platinum compounds, vinca alkaloids, and proteasome inhibitors. Preferred chemotherapeutic drugs include, but are not limited to, daunorubicin, doxorubicin, epirubicin, idarubicin, valrubicin, mitoxantrone, paclitaxel, oxaliplatin, bortezomib, paclitaxel, oxaliplatin, bortezomib, and vincristine. Anthracyclines such as doxorubicin are particularly preferred.

In a fourth aspect, the invention provides methods for manufacturing chemo-immunotherapeutic compositions comprising microparticles, a chemotherapeutic agent, and an immune adjuvant. Preferably, the chemotherapeutic agent and the adjuvant are entrapped within the microparticles. Alternatively, the chemotherapeutic agent is entrapped in the microparticles and the adjuvant is adsorbed on the surface of the particles.

The particles may be produced by methods known in the art, such as spray drying, spontaneous emulsification solvent diffusion (SESD), double-emulsion solvent-evaporation, double-emulsion solvent-evaporation, modified solvent evaporation DNA-organic phase self-emulsification (DOPSM), emulsion-diffusion-evaporation, cryopreparation, and modified phase inversion/solvent diffusion. A preferred synthetic route is a double emulsion solvent diffusion (DES-D) method (10, 11). This method is based on forming a primary reaction mixture comprising a polymeric material, the chemotherapeutic agent, the adjuvant, water, a solvent immiscible with water (chosen as detailed above in the description of the second aspect of the invention), and a first emulsifier. The primary reaction mixture is used to prepare a primary emulsion, and the primary emulsion is combined with a solution comprising water and a second emulsifier, where the second emulsifier may be the same as the first emulsifier, to form a secondary w/o/w (water/oil/water) emulsion. The water-immiscible solvent is removed from the secondary emulsion, for example by evaporation, yielding microparticles that may subjected to further processing steps, such as washing and lyophilization, as desired. In instances where it is not preferable to include the adjuvant in the primary reaction mixture, it may be instead adsorbed on the surface of the microparticles. To achieve this, the microparticles may be linked to an adsorption enhancer that increases the amount of adjuvant adsorbed on their surface.

The polymeric material is preferably biodegradable. Preferred polymeric materials include: silk, elastin, chitin, chitosan, poly($\alpha$-hydroxy acids), poly(anhydrides), and poly(orthoesters). More preferred polymeric materials include polyethylene glycol, poly(lactic acid), poly(glycolic acid), copolymers of lactic and glycolic acid, copolymers of lactic and glycolic acid with polyethylene glycol, poly(E-caprolactone), poly(3-hydroxybutyrate), poly(p-dioxanone), polypropylene fumarate, poly(orthoesters), polyol/diketene acetals addition polymers, poly(sebacic anhydride) (PSA), poly(carboxybiscarboxyphenoxyphenoxy hexone (PCPP) poly[bis(p-carboxypheonoxy)methane] (PCPM), copolymers of SA, CPP and CPM, poly(amino acids), poly(pseudo amino acids), polyphosphazenes, derivatives of poly[(dichloro)phosphazenes] and poly[(organo) phosphazenes], poly-hydroxybutyric acid, or S-caproic acid, polylactide-co-glycolide, polylactic acid, and polyethylene glycol. Polyesters are particularly preferred. Most preferred is PLGA, especially PLGA 75:25 and PLGA 85:15.

The adjuvant is preferably chosen from among ligands of membrane-bound pattern recognition receptors, or PRRs. More preferred are TLR ligands, either synthetic or derived from natural sources such as bacteria, fungi, protozoa, and viruses. Example TLR ligands include $Pam_3CSK_4$, JBT3002, OspA, Mycoplasmal Macrophage-activating Lipopeptide-2 (MALP-2), Glycosylphosphatidylinositol (GPI), Polyinosine-polycytidylic Acid (poly(I:C)), Flavolipin, Acyclic Lipid A-like Analog, Type III Repeat Extra Domain A (EDA), LMW Oligosaccharides of Hyaluronic Acid (sHA), Polysaccharide Fragments of Heparan Sulfate Host, Fusion Protein of RSV, Envelope Proteins of MMTV, Glycoinositolphospholipids (GIPLs), Lipid A, Flagellin, Mycoplasmal Macrophage-activating Lipopeptide-2 (Malp-2), Diacylated Macrophage-activating Lipopeptide-2, Diacylated Lipopeptide FSL-1, Diacylated Lipopeptide $Pam_2CSK_4$, Soluble Tuberculosis Factor (STF), Heat Shock Proteins, Imiquimod, Gardiquimod, Resiquimod (R-848), S-27610, Loxoribine, TOG, 3M-13, 3M-2, Bropirimine, CpG ODNs, AT-ODNs, and Hemozoin. More preferably, the adjuvant is a TLR-9 ligand, such as a CpG.

As set forth above in the description of the second aspect of the invention, the adjuvant may be adsorbed to the microparticles instead of being included in the primary emulsion, for example in cases where retention of the adjuvant by the microparticles is poor. Also as set forth above, the particles may be modified with adsorption enhancer, the choice of an enhancer being largely dictated by the nature of the adjuvant to be adsorbed to the microparticles.

In a fifth aspect, the present invention provides novel methods for the treatment of cancer based on the administration of a therapeutic amount of the three-component compositions of the first aspect of the invention. The methods are applicable to target a variety of malignancies, including solid tumors. Preferred target types of cancer include carcinoma, sarcoma, lymphoma, melanoma, leukemia, germ cell tumor, and blastoma. The treatment of lymphoma or melanoma is particularly preferred.

Various formulations of microparticles may be used for administration to an individual in need thereof. In some aspects, microparticles may be administered neat. In other aspects, various formulations (including any composition aspect described herein) of microparticles and a pharmaceutically acceptable excipient can be administered. Pharmaceutically acceptable excipients are known in the art. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers. Excipients as well as formulations for parenteral and nonparenteral drug delivery are set forth in Remington, The Science and Practice of Pharmacy 20th Ed. Mack Publishing (2000).

In some aspects, the microparticles are formulated for administration by injection (e.g., intratumorally, intraperitoneally, intravenously, subcutaneously, intramuscularly, etc.), although other forms of administration (e.g., oral, mucosal, via inhalation, sublingually, etc.) can be also used. Accordingly, the microparticles are preferably combined with pharmaceutically acceptable vehicles such as saline, Ringer's solution, dextrose solution, and the like. The particular dosage regimen, i.e., dose, timing and repetition, will depend on the particular individual and that individual's medical history. Generally, any of the following doses may be used: a dose of at least about 50 mg/kg body weight; at least about 10 mg/kg body weight; at least about 3 mg/kg body weight; at least about 1 mg/kg body weight; at least about 750 µg/kg body weight; at least about 500 µg/kg body weight; at least about 250 µg/kg body weight; at least about 100 µg/kg body weight; at least about 50 µg/kg body weight; at least about 10 µg/kg body weight; at least about 1 µg/kg body weight, or less, is administered. For repeated administrations over several days or longer, depending on the condition, the treatment is sustained until a desired suppression of cancer symptoms occurs. An exemplary dosing regimen comprises administering an initial dose of about 2 mg/kg, followed by a weekly maintenance dose of about 1 mg/kg, or followed by a maintenance dose of about 1 mg/kg every other week. However, other dosage regimens may be useful, depending on the pattern of pharmacokinetic decay that the practitioner wishes to achieve. Empirical considerations, such as the half-life, will contribute to determination of the dosage. The progress of this therapy is easily monitored by conventional techniques and assays.

In some individuals, more than one dose may be required. Frequency of administration may be determined and adjusted over the course of therapy. For example, frequency of administration may be determined or adjusted based on the type and severity of the cancer to be treated, whether the microparticles are administered for preventive or therapeutic purposes, previous therapy, the patient's clinical history and response to the microparticles and the discretion of the attending physician. Typically, the clinician will administer increasing dosages, until a dosage is reached that achieves the desired result. In some cases, sustained continuous release formulations of microparticles may be appropriate. Various formulations and devices for achieving sustained release are known in the art.

Dosages for microparticles may be determined empirically in individuals who have been given one or more administration(s). Individuals are given incremental doses of microparticles. To assess the efficacy of the treatment cancers cell markers can be monitored. Administration of microparticles in accordance with the treatment methods of the present invention can be continuous or intermittent, depending, for example, upon the recipient's physiological condition, whether the purpose of the administration is therapeutic or prophylactic, and other factors known to skilled practitioners. The administration may be essentially continuous over a preselected period of time or may be in a series of spaced dosages, e.g., either before, during, or after developing sepsis.

In a sixth aspect, the present invention provides novel methods for the treatment of cancer based on the administration of a therapeutic amount of the chemo-immunotherapeutic compositions of the third aspect of the invention. The methods are applicable to target a variety of malignancies, including solid tumors. Preferred target types of cancer include carcinoma, sarcoma, lymphoma, melanoma, leukemia, germ cell tumor, and blastoma. The treatment of lymphoma or melanoma is particularly preferred.

Various formulations of microparticles may be used for administration to an individual in need thereof. In some aspects, microparticles may be administered neat. In other aspects, various formulations (including any composition aspect described herein) of microparticles and a pharmaceutically acceptable excipient can be administered. Pharmaceutically acceptable excipients are known in the art. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers. Excipients as well as formulations for parenteral and nonparenteral drug delivery are set forth in Remington, The Science and Practice of Pharmacy 20th Ed. Mack Publishing (2000).

In some aspects, the microparticles are formulated for administration by injection (e.g., intratumorally, intraperitoneally, intravenously, subcutaneously, intramuscularly, etc.), although other forms of administration (e.g., oral, mucosal, via inhalation, sublingually, etc.) can be also used. Intratumoral (i.t.) injection is particularly preferred in order to induce immunogenic cell death and develop an active anti-tumor immune response, as described above. Intratumoral injection is particularly indicated in the treatment of lymphoma or melanoma.

The microparticles are preferably combined with pharmaceutically acceptable vehicles suitable for injection such as saline, Ringer's solution, dextrose solution, and the like. The particular dosage regimen, i.e., dose, timing and repetition, will depend on the particular individual and that individual's medical history. Generally, any of the following doses may be used: a dose of at least about 50 mg/kg body weight; at least about 10 mg/kg body weight; at least about 3 mg/kg body weight; at least about 1 mg/kg body weight; at least about 750 µg/kg body weight; at least about 500 µg/kg body weight; at least about 250 µg/kg body weight; at least about 100 µg/kg body weight; at least about 50 µg/kg body weight; at least about 10 µg/kg body weight; at least about 1 µg/kg body weight, or less, is administered. For repeated administrations over several days or longer, depending on the condition, the treatment is sustained until a desired suppression of cancer symptoms occurs. An exemplary dosing regimen comprises administering an initial dose of about 2 mg/kg, followed by a weekly maintenance dose of about 1 mg/kg, or followed by a maintenance dose of about 1 mg/kg every other week. However, other dosage regimens may be useful, depending on the pattern of pharmacokinetic decay that the practitioner wishes to achieve. Empirical considerations, such as the half-life, will contribute to determination of the dosage. The progress of this therapy is easily monitored by conventional techniques and assays.

In some individuals, more than one dose may be required. Frequency of administration may be determined and adjusted over the course of therapy. For example, frequency of administration may be determined or adjusted based on the type and severity of the cancer to be treated, whether the microparticles are administered for preventive or therapeutic purposes, previous therapy, the patient's clinical history and response to the microparticles and the discretion of the attending physician. Typically, the clinician will administer increasing dosages, until a dosage is reached that achieves the desired result. In some cases, sustained continuous release formulations of microparticles may be appropriate. Various formulations and devices for achieving sustained release are known in the art.

Dosages for microparticles may be determined empirically in individuals who have been given one or more administration(s). Individuals are given incremental doses of microparticles. To assess the efficacy of the treatment cancers cell markers can be monitored. Administration of microparticles in accordance with the treatment methods of the present invention can be continuous or intermittent, depending, for example, upon the recipient's physiological condition, whether the purpose of the administration is therapeutic or prophylactic, and other factors known to skilled practitioners. The administration may be essentially continuous over a preselected period of time or may be in a series of spaced dosages, e.g., either before, during, or after developing sepsis.

With respect to all methods described herein, reference to the microparticles of the invention also include compositions comprising one or more of such particles. These compositions may further comprise suitable excipients, such as pharmaceutically acceptable excipients including buffers, which are well known in the art. The present invention can be used alone or in combination with other conventional methods of treatment.

Example Three-Component Compositions

Ovalbumin (OVA) was chosen as the example antigen. CpG and Poly (I:C) were chosen as example TLR-9 and TLR-3 ligand adjuvants. The example polymer of choice was a poly(lactic-co-glycolic acid) (PLGA) polymer having a lactide:glycolide ratio of 75:25 and an unmodified ester end group.

The study included two parts, the first part involving the preparation, optimization and characterization of the microparticles. The following five types of formulation were manufactured: (1) OVA-loaded on PLGA microparticles MP; (2) OVA and Poly (I:C) "co-loaded" on PLGA MP; (3) OVA and CpG co-loaded on PLGA MP; (4) OVA, CpG, and Poly (I:C) "tri-component" co-loaded on PLGA MP; and (5) OVA, CpG, and OVA in soluble form without microparticles. The "co-loaded" particles included OVA and one adjuvant chosen from CpG or Poly(I:C). The "tri-component" particles included both adjuvants. Preparation (5) was chosen to test the hypothesis of whether a particulate carrier is essential to elicit the strongest immune response. The second part involved in vivo studies on the efficacy of the preparations in prophylactic and therapeutic murine tumor models. The outline of the in vivo study is illustrated in FIG. 1.

Preparation of OVA-Loaded, OVA+Poly (I:C) Co-Loaded, and OVA+CpG Co-Loaded PLGA Microparticles The polymer of choice was poly(lactic-co-glycolic acid) (PLGA) with a lactide:glycolide ratio of 75:25, an unmodified ester end group, a medium MW grade, and an inherent viscosity of 0.51 dL/g. The antigen, either separately or admixed with either CpG or Poly (I:C), was dissolved in 300 μL of 1% poly vinyl alcohol (PVA). The resulting solution was sonicated together with 3 mL of polymer dissolved in dichloromethane (DCM) with an ultra sonicator probe for 30 seconds. The resulting primary emulsion was then rapidly homogenized at 9500 rpm for 30 seconds into 30 mL of 1% PVA solution to form a secondary w/o/w (water/oil/water) emulsion. Stirring was continued following homogenization until complete evaporation of the DCM. The resulting microparticles were collected by centrifugation, washed twice, and lyophilized overnight.

Figure 2:
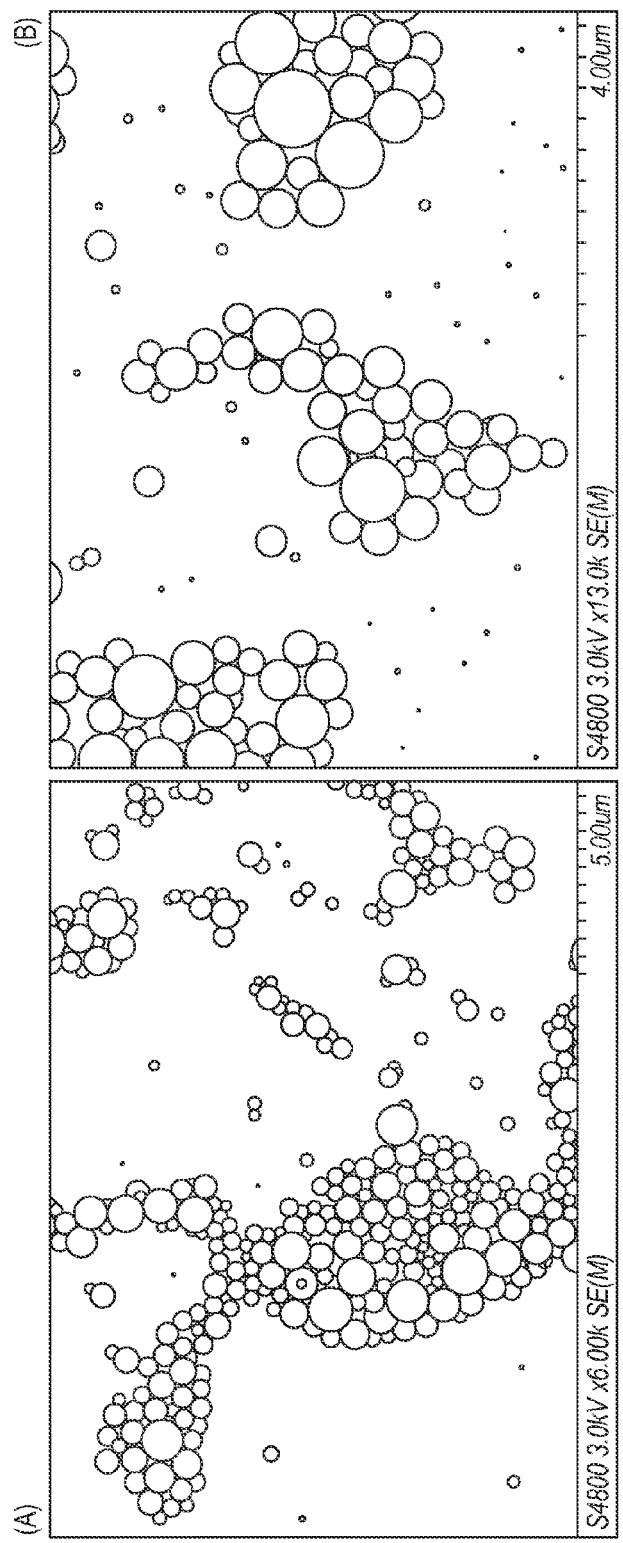
FIG. 2 includes SEM images of (A) OVA+Poly (I:C) co-loaded PLGA particles and (B) OVA+CpG co-loaded PLGA microparticles. The particles exhibit a spherical shape with smooth surface morphology with a particle size in the range of 1-5 µm.
Figure 3:
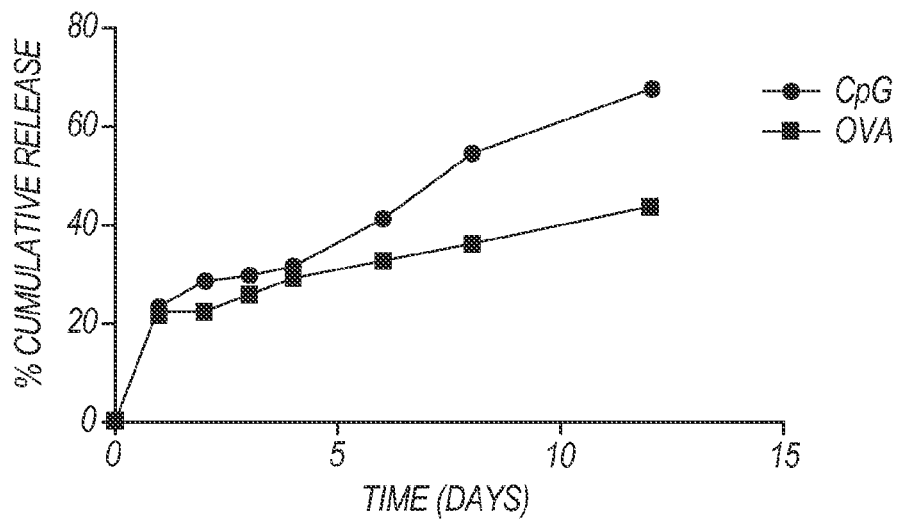
FIG. 3 illustrates in vitro release profiles of OVA, Poly (I:C) and CpG from their respective co-delivery PLGA carriers.
Figure 3:
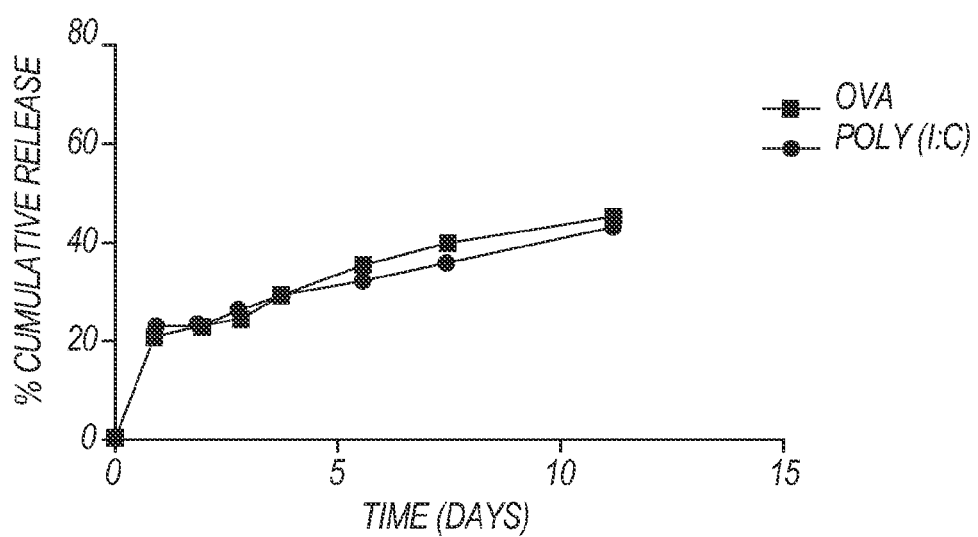

The particles were characterized for particle size and entrapment efficiency and to study in vitro release profiles. Ovalbumin (OVA) was analyzed using a micro-BCA assay kit. CpG and Poly (I:C) were analyzed using OliGreen (Molecular Probes, Eugene, Oreg.) by fluorescence spectroscopy and RP-HPLC. The preparation of microparticles (1) and co-loaded microparticles (2)-(3) was successfully carried out using the above double emulsion-solvent evaporation technique. The SEM images of such particles are illustrated in FIG. 2. The characteristics of microparticles (1)-(3) has been summarized in Table 1, below, and release profiles are illustrated in FIG. 3, where it can be seen that all the components exhibited an initial burst release followed by a more controlled release.

Next, tri-component microparticles (5), i.e. microparticles co-delivering the antigen and two adjuvants, were prepared. Following the method used in the preparation of microparticles (1)-(3), CpG tended to leach out into the water phase, thereby resulting in an entrapment efficiency of less than 3%, and therefore in a very cost-ineffective process.

Figure 4:
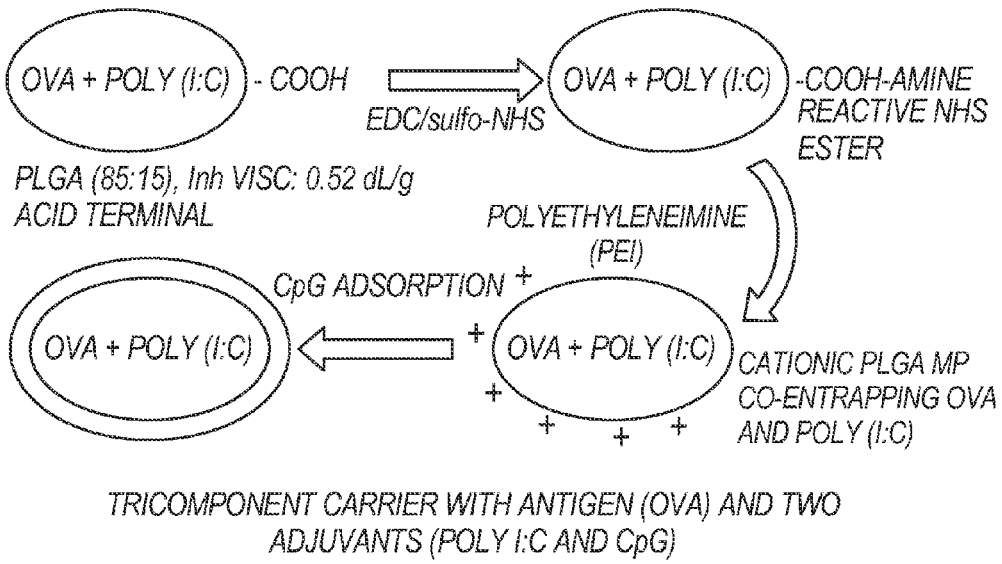
FIG. 4 illustrates a scheme of fabrication for novel tri-component PLGA microparticle carrier for co-entrapping antigen OVA and two adjuvants CpG and Poly (I:C).

Hence, an alternative approach to co-load the three components together was developed, leading to a novel microparticle carrier system, which co-delivers all the three components simultaneously. The scheme of this novel synthesis is illustrated in FIG. 4. The polymer of choice was PLGA with a lactide:glycolide ratio of 85:15, an inherent viscosity of 0.62 dL/g, and a carboxylic acid (—COOH) end groups for further modifications. Poly (I:C) and OVA were co-loaded within the microparticles using the same method as described for microparticles (1)-(3). The resulting co-loaded microparticles were then analyzed for size and entrapment efficiency.

Following lyophilization, the particles were prepared for the conjugation of a cationic polymer on the surface by reacting with EDC-NHS. 100 mg of the particles were suspended in 3 mL MES buffer (pH 5.5), and a 20-fold molar excess of both EDC and NHS over PLGA was used for modification. The EDC and NHS were each dissolved in 1 mL MES buffer and were slowly added to the particles under constant stirring. Stirring was continued for 1 hour. The particles were then centrifuged and washed twice with PBS to remove any unreacted EDC-NHS.

The particles were then suspended in 3 mL of autoclaved PBS buffer. A 10-fold molar excess of polyethyleneimine (PEI), a cationic polymer, was used for conjugation to the surface and for imparting an overall positive charge to the OVA and Poly (I:C) co-loaded PLGA particles. The PEI was suspended in 2 mL PBS. The particles were then added drop wise into the PEI solution under constant stirring and the reaction was allowed to proceed at room temperature for 2 hours. The particles were then collected by centrifugation, washed and lyophilized overnight.

The particles were analyzed for OVA and Poly (I:C) content to account for any loss of by diffusion during the modification steps. The results of this modification have been listed in Table 1. PEI conjugation was confirmed by a change in zeta potential from a slightly negative charge to a distinct positive charge. The particles were then incubated with a 5 mg/mL solution of CpG for 30 minutes to allow surface adsorption of CpG to the now cationic particles, yielding the tri-component particles.

The zeta potential of the OVA and Poly (I:C) co-loaded cationic particles before and after modification with PEI is illustrated in Table 2, below. Following PEI modification, the particles retained 80% of the entrapped OVA and Poly (I:C), with only a 15-20% loss of entrapped components during modification, while the CpG binding efficiency was 50%.

TABLE 1

Characterization of entrapment efficiency of single component and co-delivery PLGA MP carriers.

| Group | Entrapment Efficiency (% ± SD) | | |
|---|---|---|---|
| | OVA | Poly (I:C) | CpG ODN |
| OVA | 62.3 ± 2.23 | — | — |
| OVA + Poly (I:C) | 52.0 ± 3.14 | 41.2 ± 1.45 | — |
| OVA + CpG | 50.14 ± 2.17 | — | 22.5 ± 2.01 |

TABLE 2

Characterization of the novel tri-component PLGA MP carrier system co-delivery antigen (OVA) and two adjuvants CpG and Poly (I:C)

| Zeta Potential (mV ± SD) | | |
|---|---|---|
| Unmodified | After PEI Conjugation | After CpG Adsorption |
| −40.1 ± 3.4 | 27.3 ± 4.1 | −17.2 ± 4.6 |

| Content μg OVA/mg PLGA MP | | Content μg Poly (I:C)/mg PLGA MP | |
|---|---|---|---|
| Before PEI Conjugation | After PEI Conjugation | Before PEI Conjugation | After PEI Conjugation |
| 20.18 | 16.8 | 7.1 | 5.1 |

In Vivo Studies

Figure 5:
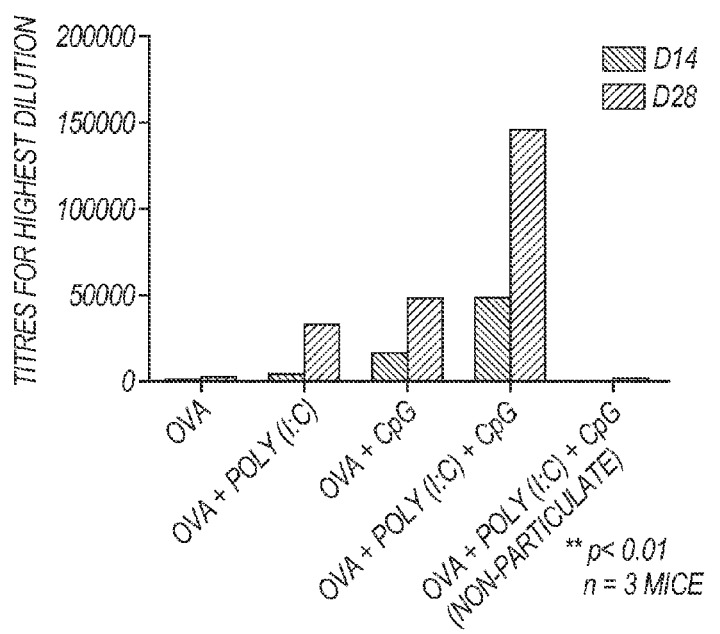
FIG. 5 illustrates Anti-OVA IgG2a response of mice vaccinated with various treatment groups in a prophylactic tumor model. Serum samples were analyzed by ELISA on Day 14 and Day 28 post vaccination to quantify IgG2a response.

The antibody response in mice upon intraperitoneal administration of microparticles is reported in FIG. 5. Mice vaccinated with microparticles entrapping OVA alone elicited a weak IgG2a response. The IgG2a levels were three to four-fold higher for mice vaccinated with microparticles co-entrapping CpG ODN or Poly (I:C) with OVA. The tri-component particles generated the strongest response, which was three-fold higher than that induced by the co-delivery particles, a fact indicative of an operative synergy between the two adjuvants. The same tri-component formulation in the absence of the microparticles failed to trigger any immune response, indicating the necessity of a delivery system for an effective immune response.

Figure 6:
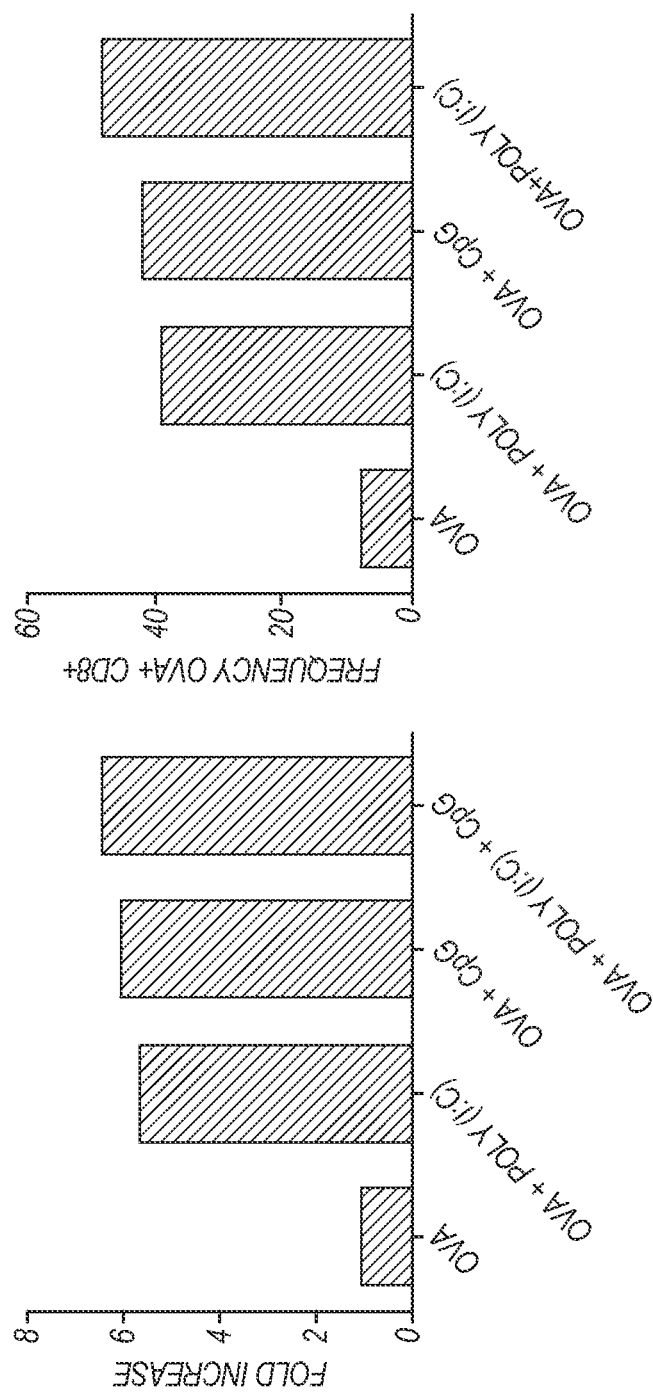
FIG. 6 illustrates CD8+ (Cytotoxic T-cell response) in mice vaccinated with various treatment groups in a prophylactic tumor model. Peripheral blood lymphocytes were analyzed using flow cytometry to enumerate the frequency of antigen (OVA+) CD8+T-lymphocytes.

These results also indicate that a co-delivery of antigen and an adjuvant is essential to generate a strong $T_H$-1 type immune response. The IgG2a response which is a surrogate marker for a $T_H$-1 polarized immune response also showed a progressive increase in levels from day 14 to day 28. These responses indicated that the microparticulate formulations co-entrapping the antigen and TLR ligand adjuvant(s) are able to generate a $T_H$-1 biased immune response and to maintain high levels of antibody response for a prolonged period, a critical feature in tumor therapy. A similar trend was observed in the generation of antigen-specific T-cell response, where the maximum response was generated by the co-delivery and tri-component vehicles (FIG. 6).

For prophylactic tumor studies, male C57Bl/6 mice were subjected to an immunization schedule with microparticles (1)-(4). A first vaccination was administered on day 0 of the study, followed by a booster on day 14. On day 28, the mice were injected with 107 EG-7 tumor cells subcutaneously on the right flank. EG7 cells are derived from the murine T-cell lymphoma EL4 transfected with cDNA for stable expression of ovalbumin. The ability of the microparticles to suppress tumor growth was studied by measuring tumor volume following the tumor challenge. This was carried out according to a method described by Lubaroff et al. for studying tumor volume by measuring its height, width and depth and making corrections for an ellipsoidal shape of the tumor.

Figure 7:
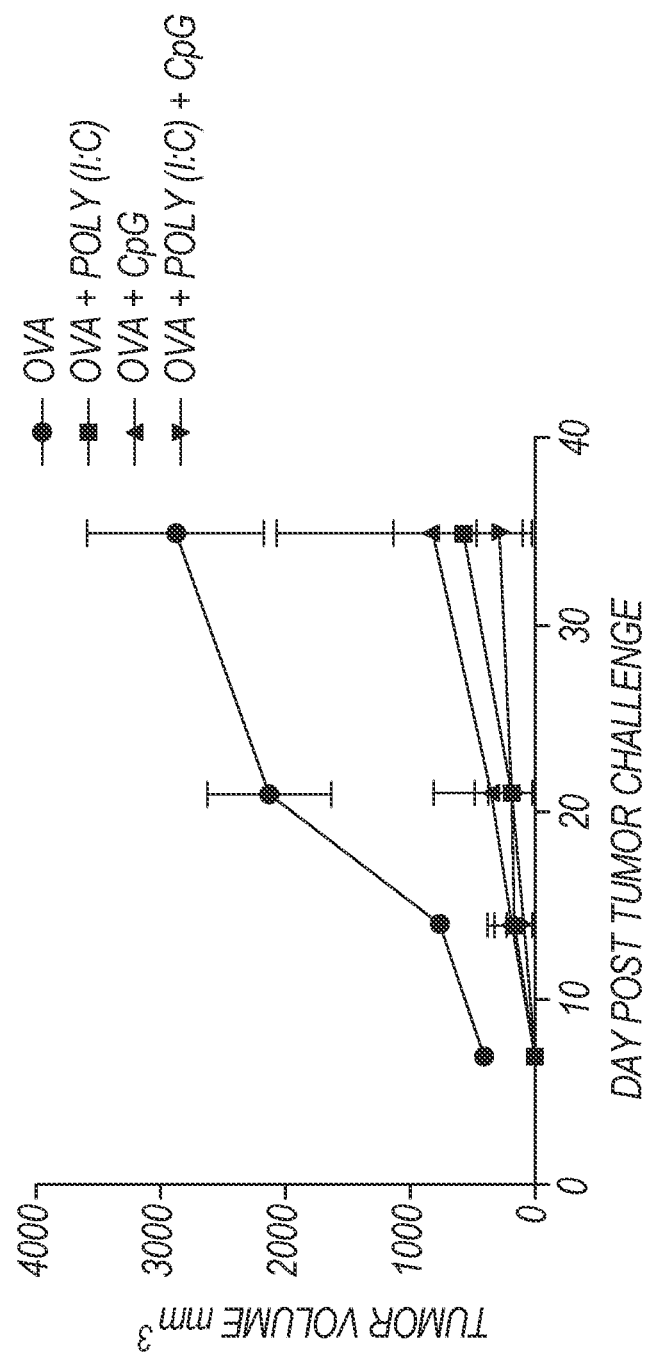
FIG. 7 illustrates tumor growth progression in mice vaccinated with various treatment groups in a prophylactic tumor model.

The results of the tumor challenge up to day 35 are reported in FIG. 7. Mice vaccinated with OVA alone showed the most aggressive, high exponential slope of tumor growth. The co-delivery vehicles induced a significantly slower rate of tumor progression, whereas the tri-component group showed the maximal resistance to aggressive tumor growth with the smallest tumor volumes recorded in the study. Without being bound to any particular theory, these results are indicative of a synergistic mechanism between the TLR ligands in suppressing tumor growth.

Example Chemo-Immunotherapeutic Compositions

Attempts to co-deliver doxorubicin and CpG in the same liquid formulation were unsuccessful because the two compounds, when mixed, readily crashed out of solution, forming a precipitate. In addition, mixtures featuring the two compounds, when tested in the treatment of cancer, exhibited lower therapeutic efficacy than doxorubicin alone (data not shown). Without being bound to any particular theory, it is believed that the formation of the precipitate is due to electrostatic interactions between the negative charges of CpG and the positive charges of doxorubicin. In an attempt to circumvent this problem, the co-delivery vehicle of doxorubicin and CpG was attempted by means of microparticle carriers.

Experiment 1: Preparation of Doxorubicin-Loaded PLGA Microparticles

Doxorubicin is commercially available as water soluble HCl salt (Sigma-Aldrich, St Louis, Mo.), and is suited to microparticle fabrication by double emulsion solvent-evaporation approach. The example polymer of choice was poly (lactic-co-glycolic acid) (PLGA) with a lactide:glycolide ratio of 50:50, and an unmodified ester end group. The polymer used was a low molecular weight grade with an inherent viscosity of 0.2 dL/g.

Five mg of doxorubicin HCl were dissolved in 500 μL of 1% polyvinyl alcohol (PVA). This solution was sonicated using an ultra sonicator probe with 5 mL of polymer dissolved in DCM for 30 seconds. The resulting primary emulsion was then rapidly homogenized at 9500 rpm for 30 seconds into a 50 mL of 1% PVA solution to form the secondary w/o/w (water/oil/water) emulsion. Stirring was continued following homogenization until complete evaporation of the DCM. The formed microparticles were collected by centrifugation, washed twice, and lyophilized overnight. The particles were characterized for particle size and entrapment efficiency.

Analysis of Doxorubicin

Doxorubicin is an anthracycline compound, a feature rendering it a good fluorophore owing to its cyclic aromatic ring. Doxorubicin was analyzed by dissolving a known quantity of drug in either water or dimethyl sulfoxide (DMSO), and a serial dilution of the drug was made in both solvents. The drug solutions were then assayed using fluorescence spectroscopy by setting the excitation and emission wavelengths at 490 and 585 nm, respectively, on a Spectra ax Fluorescence plate reader. A standard curve, as described above, was constructed for doxorubicin for further analysis of entrapment efficiencies following microparticulate fabrication.

Analysis if Entrapment Efficiency (EE) and Loading Efficiency (LE) of Dox-Loaded PLGA Particles The supernatants after microparticle fabrication were analyzed using fluorescence spectroscopy to determine the amount of un-entrapped doxorubicin and thus calculate the entrapment efficiency (EE) of doxorubicin-loaded PLGA microparticles. The loading efficiency was calculated by dissolving a known quantity of lyophilized microparticles in DMSO and the resulting solution was analyzed by fluorescence spectroscopy. EE and LE were both assessed to ensure the accuracy of the analytical techniques.

Figure 8:
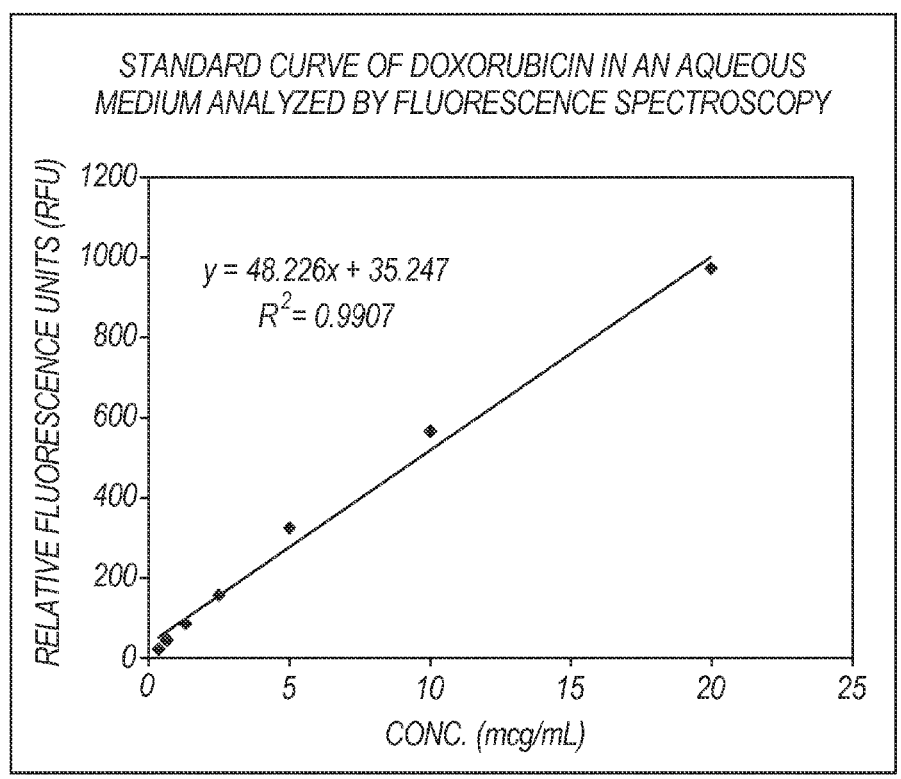
FIG. 8 illustrates a standard curve of doxorubicin in an aqueous medium analyzed by fluorescence spectroscopy.
Figure 9:
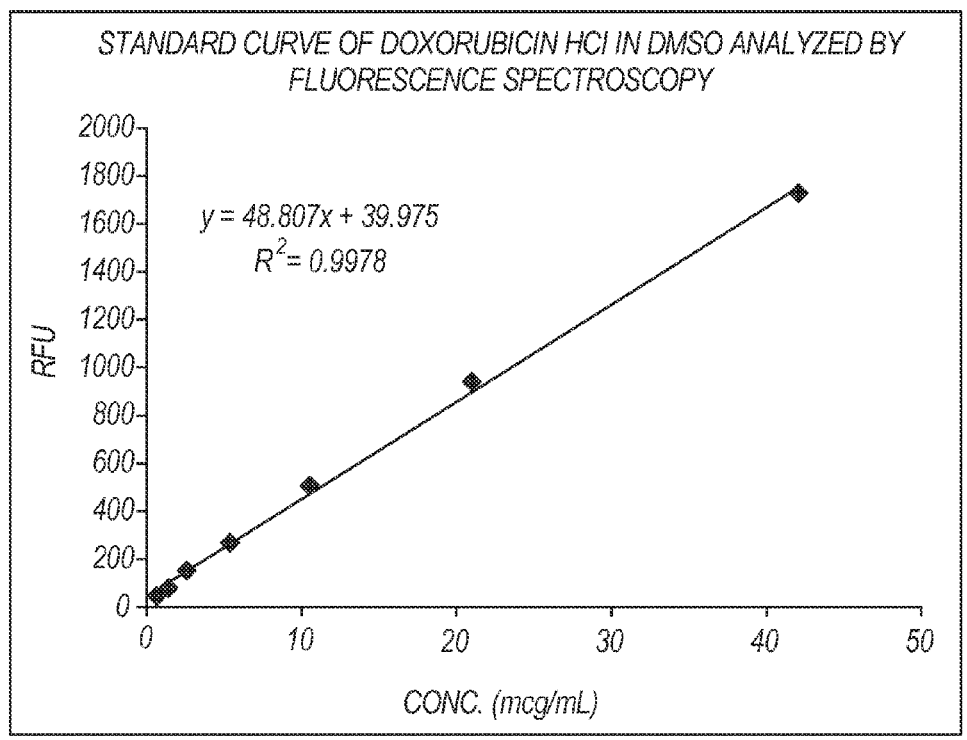
FIG. 9 illustrates a standard curve of doxorubicin in DMSO analyzed by fluorescence spectroscopy.
Figure 10:
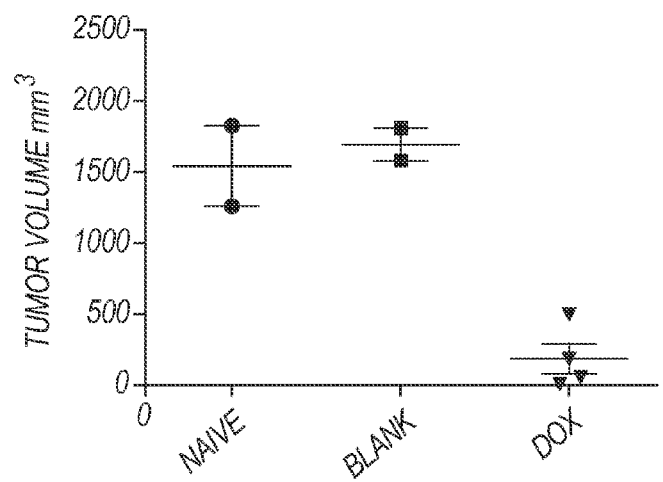
FIG. 10 illustrates inhibition of EL4 tumor growth by i.t. injection of Dox MP.

FIGS. 8 and 9 illustrate the standard curve of doxorubicin analyzed by fluorescence spectroscopy in water and DMSO as solvents. The doxorubicin-loaded PLGA particles showed a mean particle size of 1.5 μm and EE of 33% and LE of 32%. A good mass balance between LE and EE indicated that both the techniques were effective in calculating the entrapment efficiencies of dox-loaded microparticles.

Improving Doxorubicin Entrapment Efficiency

Without being bound to any particular theory, since doxorubicin is usually provided as a salt, it is believed that the high water solubility results in a high extent of diffusion of doxorubicin into the external phase during fabrication, thereby resulting in low entrapment efficiency (EE). To test this hypothesis, the polymer grade was changed with the objective of improving the EE. The new polymers were both PLGA with a lactide:glycolide ratio of 75:25 and 85:15, respectively.

The 75:25 grade PLGA had an inherent viscosity of 0.2 dL/g and the 85:15 grade PLGA had an inherent viscosity of 0.62 dL/g. The purpose of using the higher lactide to glycolide ratio was to investigate the effect of crystallinity and hydrophobicity on the EE of doxorubicin-loaded PLGA microparticles. Without being bound to any particular theory, it is believed that the higher degree of hydrophobicity of the internal organic phase during polymer fabrication ensures a greater diffusional resistance to the hydrophilic drug, thus improving EE.

Fabrication of Doxorubicin- and CpG Co-Entrapped Microparticles

Five mg of doxorubicin HCl were dissolved in 300 μL of 1% PVA, and a CpG ODN solution in PBS (10 mg/ml) was admixed with the doxorubicin solution to form the internal aqueous phase. The resulting solution was then sonicated with an ultra sonicator probe together with 5 mL of polymer (PLGA, lactide:glycolide ratio of 75:25, inherent viscosity 0.15 dL/g) dissolved in dichloromethane (DCM) for 30 seconds. The resulting primary emulsion was then rapidly homogenized at 9500 rpm for 30 seconds together with 50 mL of 1% PVA solution to form a secondary water in oil in water (w/o/w) emulsion. Stirring was continued following homogenization until complete evaporation of the DCM. The resulting microparticles were collected by centrifugation and washed twice and lyophilized overnight. The particles were then characterized for particle size and entrapment efficiency.

The amino groups of doxorubicin render the compound basic and usually protonated in aqueous media. Conversely, CpG bears an overall negative charge owing to the phosphate back bone typical of an oligodeoxynucleotide. Upon addition of CpG to a solution of doxorubicin in 1% PVA for microparticle fabrication, there was instant precipitation believed to be due to the interaction of two oppositely charged species, resulting in either the formation of salts or the instant precipitation of doxorubicin from solution due to change in pH and reduction in solubility.

To ensure adequate entrapment of both molecules, it is desirable to have both drugs in high amounts in the lowest possible volume of internal aqueous phase. Mixing dilute solutions of the two drugs to avoid charge interaction may however yield an unsatisfactory EE. To overcome this limitation, the fabrication of cationic PLGA particles entrapping doxorubicin with CpG adsorbed on the surface was undertaken.

Fabrication of Novel Combined Chemo-Immunotherapeutic Vehicle for Co-Delivering Doxorubicin and CpG The polymer of choice was PLGA having a lactide:glycolide ratio of 85:15, an inherent viscosity of 0.62 dL/g and with a carboxylic acid (—COOH) end group for further modifications. The method of fabrication remained the same as described in Experiment 2. The particles were analyzed for size and entrapment efficiency. Following lyophilization, the particles were modified using EDC-NHS for conjugation of a cationic polymer on the surface. 100 mg of the particles were suspended in 3 mL MES buffer (pH 5.5). A 20-fold molar excess of EDC and NHS over PLGA were each dissolved in 1 mL MES buffer and were slowly added to the particles under constant stirring. Stirring was continued for 1 hour. The particles were then centrifuged and washed twice with PBS to remove any unreacted EDC-NHS.

The particles were then suspended in 3 mL of autoclaved PBS. A 10-fold molar excess of the cationic polymer polyamidoamine (PAMAM) relative to particle concentration was used for surface conjugation and imparting an overall positive charge to the doxorubicin-loaded PLGA particles. The cationic polymer was suspended in 2 mL PBS. The particles were then added dropwise into the PAMAM solution under constant stirring and the reaction was allowed to proceed at room temperature for 2 hours. The particles were then collected by centrifugation, washed and lyophilized overnight. The particles were then analyzed for doxorubicin content to account for any loss of doxorubicin by diffusion during the modification steps. PAMAM conjugation was confirmed by a change in zeta potential from a slightly negative charge to a distinct positive charge (data not shown).

The particles were then incubated with a 5 mg/mL solution of CpG for 30 minutes to allow surface adsorption of CpG to the cationic particles. The particles were collected by centrifugation and the supernatant was analyzed for unadsorbed CpG by oligogreen assay to determine the amount of CpG adsorbed/mg of PLGA particles.

Results

It can be observed that the zeta potential of the PLGA particles prior to modification with PAMAM was not as negative as one would have expected with PLGA with a COOH end group (data not shown). Without being bound to any particular theory, this can be attributed to the fact that during entrapment of doxorubicin within PLGA particles, some amount of doxorubicin also remained associated with the surface of the particles providing the initial burst release. It is thus believed that the surface-associated cationic doxorubicin left the particles with an overall lower amount of negative charge. However, it can be seen that upon PAMAM conjugation, the particles exhibited a distinct positive charge. It can be further observed that upon CpG adsorption on the surface the particles reverted back to being negatively charged, likely owing to the phosphate back-bone on CpG that imparts an overall negative charge to the particles.

It can be observed that, after PAMAM modification, the particles retained 90% of the entrapped doxorubicin with only 10% loss of entrapped doxorubicin during entrapment. The overall loading of doxorubicin and CpG was 12 μg and 30 μg of CpG per mg of PLGA particles.

Comparing Dox MP to Doxorubicin

PLGA microparticles ("MP") containing doxorubicin ("Dox MP") were produced using a DES-D method as illustrated above. Careful control over the stirring speed and surfactant concentration yielded particles of various sizes from 200 nm and larger containing up to 8 micrograms (μg) of doxorubicin per milligram (mg) of particles.

Dox MP are Taken UP by Cells, Induce Expression of Calreticulin, and Cause Cell Death In Vitro Dox MP or soluble doxorubicin were added to malignant B cell lines, and images obtained by means of confocal microscopy. Soluble doxorubicin was visible in the nucleus, whereas Dox MP were present in the cytoplasm. As discussed above, expression of calreticulin is a marker of immunogenic cell death. Dox MP were more effective at inducing expression of calreticulin by A20 B cell lymphoma cells than was soluble doxorubicin at the same concentration. The soluble doxorubicin and the Dox MP had similar anti-proliferative effects in vitro, although the kinetics of the cytotoxic effect of the Dox MP was slower than that seen with soluble doxorubicin (data not shown).

Non-cytotoxic microparticles remain in the tumor, peritumoral environment and draining lymph node for up to a week after intratumoral (i.t.) injection in murine lymphoma. C57BL/6 mice were inoculated subcutaneously with EL4 T cells. Similar studies were done with Balb/C mice and A20 B cell lymphoma cells. When the tumors reached 0.5 cm in size, they were injected with rhodamine-labeled MPs in 0.5 ml buffer. Mice were sacrificed at various time points and tumors evaluated histologically and by transmission electron microscopy. Tumor cell uptake of Dox MP was observed within 24 hours of i.t. injection. MPs were identifiable in the tumor and draining lymph nodes up to 7 days following i.t. injection (data not shown).

Dox MPs have Local Anti-Tumor Activity

Mice bearing subcutaneous lymphoma were injected i.t. with a single dose of Dox MPs containing 0.1 mg doxorubicin in 12.5 mg MPs and tumor growth was followed. Tumors treated with Dox MP were significantly smaller at day 21 (FIG. 11) and there was no evidence of ulceration or skin breakdown over the injected sites or other evidence of toxicity.

Assessing the Effect of In Situ Injection of MPs Containing Both Doxorubicin and the TLR9 Agonist CpG ODN on Lymphoma Cells, the Immune Microenvironment, and the Anti-Lymphoma Immune Response The Effect of CpG ODN is Most Pronounced Locally Extensive preclinical data in a variety of settings and systems indicates peritumoral injection of CpG ODN has a greater ability to induce an active anticancer immune response than systemic therapy (23, 24). Intradermal CpG ODN can also induce activation of dendritic cells in sentinel lymph nodes of melanoma patients (25). These findings are consistent with the results of a CLL trial where subjects received a single dose of CpG ODN either i.v. or s.q. Higher doses of i.v. therapy resulted in changes in CLL cell phenotype. In contrast, with s.q. therapy, local but transient inflammation was noted at the site of injection and in draining nodes, even at lower doses. Together, these data support i.t. delivery of CpG ODN, based on both the direct effects on malignant B cells, and effects on benign infiltrating aspects of the immune system.

CpG ODN for In Situ Immunization in Lymphoma

Levy and colleagues evaluated in situ immunization with CpG ODN in both murine models and clinical trials. In a murine model, successful development of an anti-lymphoma immune response was found when i.t. injection of CpG ODN was combined with systemic chemotherapy (15). The results of a phase I/II clinical study of in situ immunization CpG ODN in patients with lymphoma (2) were reported. In this clinical trial, soluble CpG ODN was injected i.t into nodes that had been treated with low dose radiation. Four of 15 subjects had a PR or CR, including regression of untreated sites, and vaccination induced tumor-reactive memory T cells in a number of subjects.

Soluble CpG ODN and Doxorubicin are Synergistic

Figure 11:
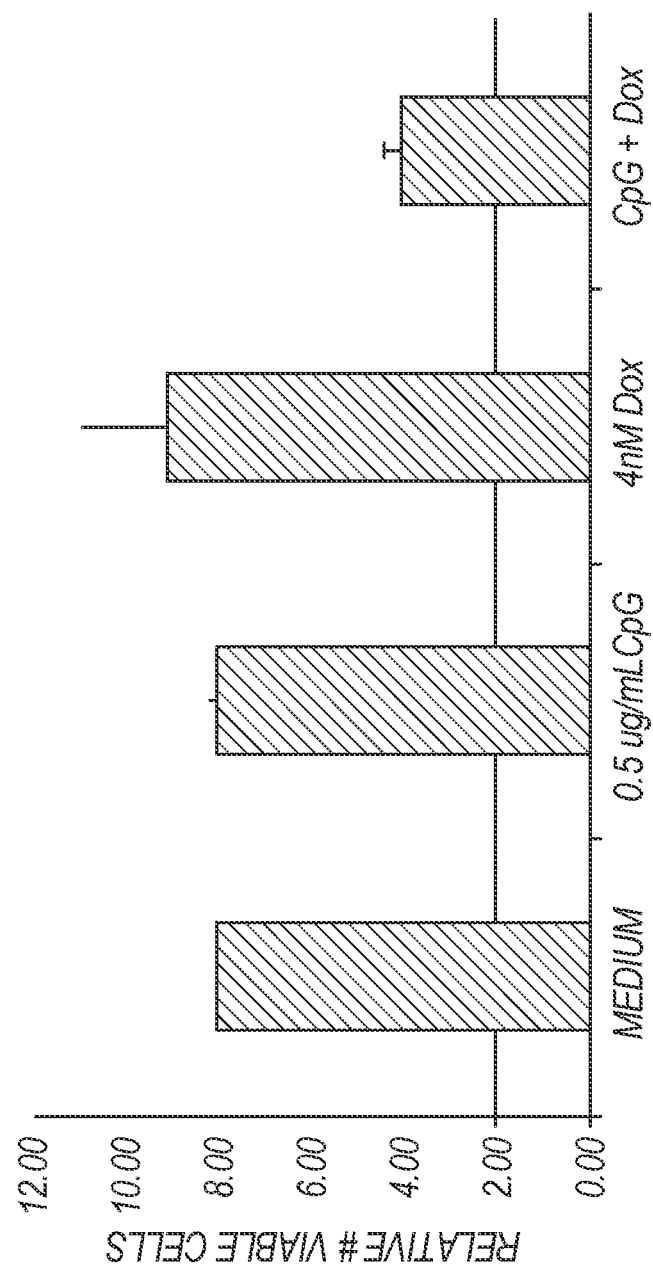
FIG. 11 illustrates relative numbers of viable CD19+ cells after treatment with doxorubicin and CpG ODN.

Pilot studies exploring the combination of soluble CpG ODN and doxorubicin were conducted (FIG. 11). This combination resulted in synergistic killing of a number of malignant B cells, including A20 murine lymphoma cells and primary CLL cells.

Formulation of Particles Comprising CpG and Doxorubicin ("CpG Dox MPs")

As stated above, doxorubicin has a negative charge while CpG ODN has a positive charge which impacts on production of NP containing both agents. A number of approaches to producing CpG Dox MPs were then evaluated. The first approach was to coat Dox MPs with CpG ODN on the surface. The surface positive charge resulted in a change in physical properties for these particles that led to aggregation. A second approach involved mixing doxorubicin and CpG ODN in aqueous solution to allow for formation of nanocomplexes, and then incorporating the nanocomplexes into NP. This was effective but only over a limited range of ratios of doxorubicin to CpG. Finally, doxorubicin and CpG ODN were independently emulsified in polymer solution, then combined and emulsified into final PLGA MPs that contained both agents. PLGA MPs loaded with doxorubicin and CpG displayed smooth and spherical morphologies with low polydispersities and reproducible loading levels of doxorubicin and CpG. This approach also afforded the most control over concentrations of doxorubicin and CpG ODN.

Therapeutic Effect of MP Containing Both Doxorubicin and CpG (CpG Dox MP)

Figure 12:
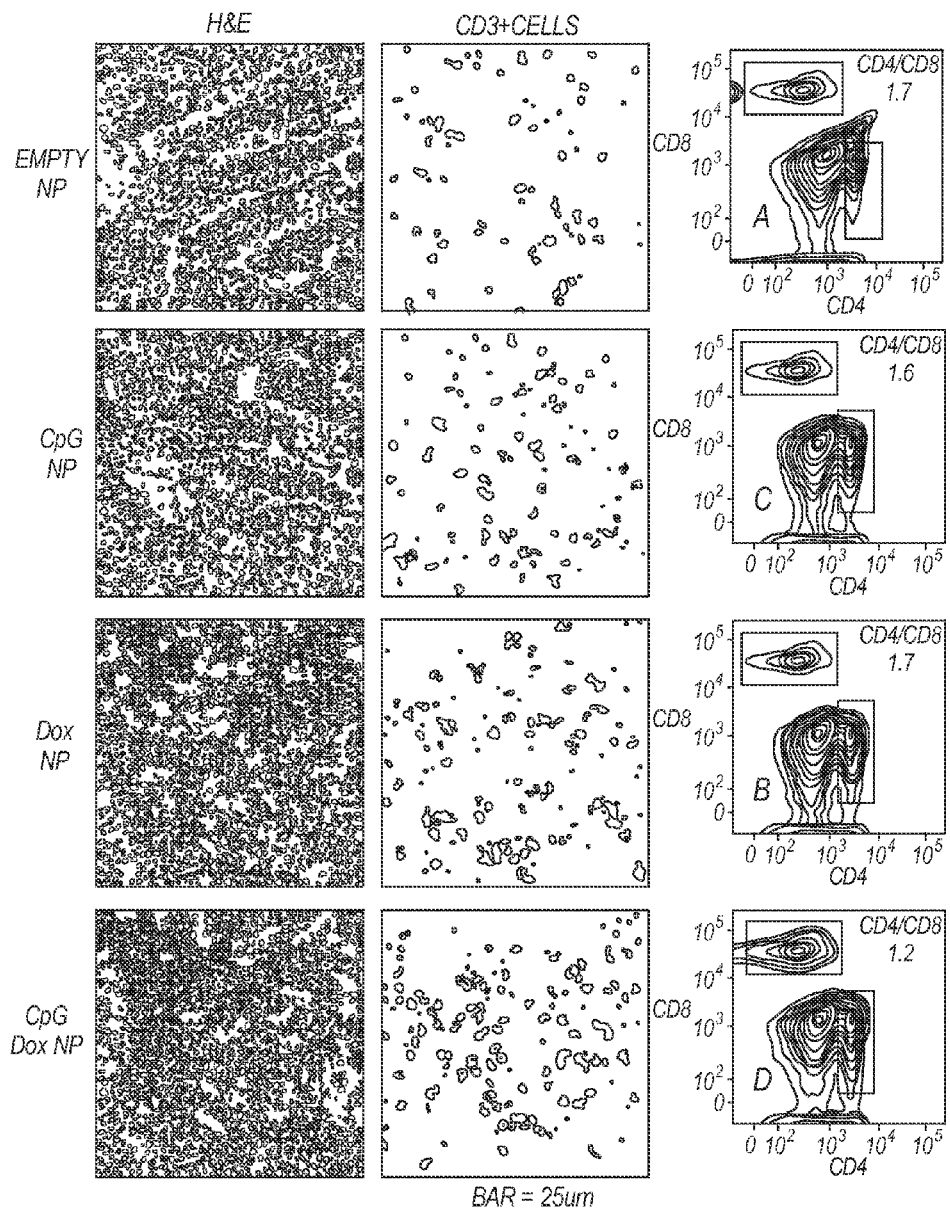
FIG. 12 illustrates histology and immunophenotype of A20 tumors one week after i.t. injection with MP (here labeled as NP).
Figure 13:
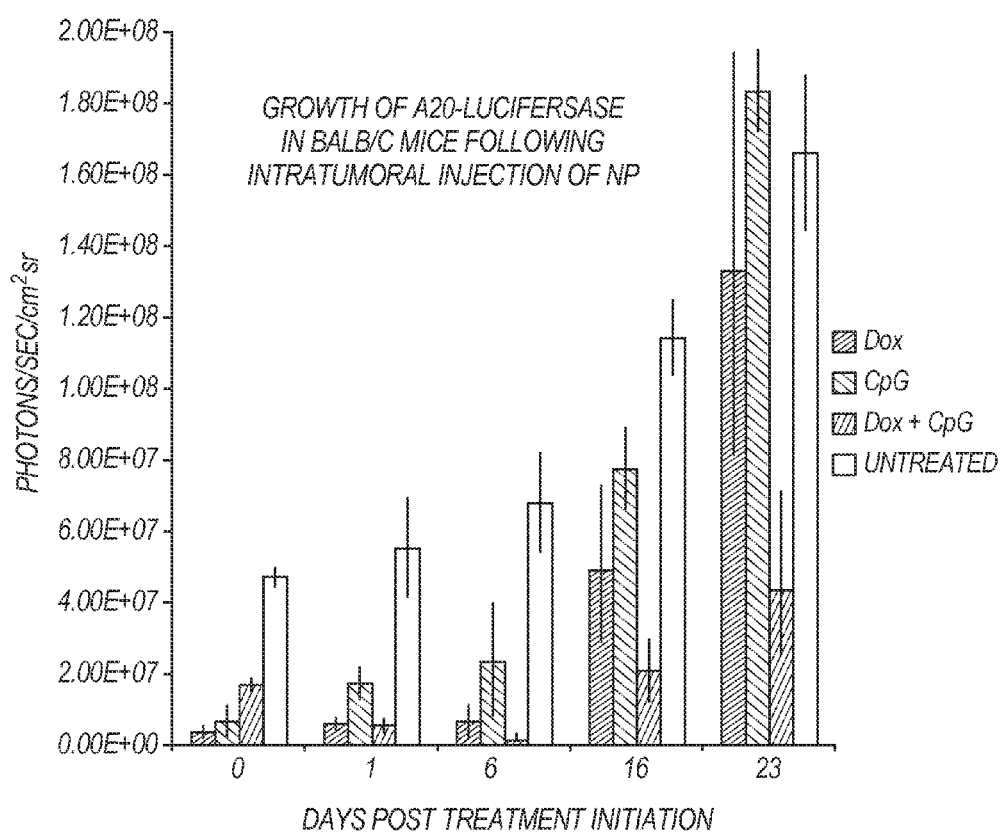
FIG. 13 illustrates the growth of A20-luciferase in Balb/C Mice following i.t. injection of MP.

Pilot studies were conducted evaluating CpG Dox MP in the A20 model. These studies included evaluation of tumor histology and immunophenotype of intratumoral T cells one week after i.t. injection with the MP. As illustrated in FIG. 12, increased numbers of infiltrating lymphocytes were found after injection of MP containing dox. The absolute and relative number of intratumoral CD8 cells increased following injection with CpG Dox MP. In a separate study, CpG Dox MP were found to be superior to particles containing either agent alone (at equivalent concentrations) in their ability to induce regression of the injected luciferase-expressing A20 cells (FIG. 13).

Together, the foregoing results suggest MP containing doxorubicin enhances infiltration into the tumor of lymphocytes and MP containing CpG ODN increase the number of CD8 cells. MP containing both doxorubicin and CpG ODN enhance tumor regression. Similar results were seen with EL4 lymphoma. Mice with complete regression of EL4 after therapy were rechallenged with the same lymphoma. Tumors grew more slowly in mice that had received prior therapy with CpG Dox MP than those treated with Dox MP. The numbers of animals in this rechallenge pilot study were small. Nevertheless, this preliminary data suggests CpG Dox MPs can not only induce lymphoma regression, but may lead to development of an anti-lymphoma immune response and enhanced protection against rechallenge. It should be noted that these pilot studies were done with CpG Dox MP that have not yet been optimized with respect to parameters such as size, doxorubicin concentration and CpG ODN concentration.

In view of the above, it will be seen that several advantages of the invention are achieved and other advantageous results attained.

Not all of the depicted components illustrated or described may be required. In addition, some implementations and embodiments may include additional components. Variations in the arrangement and type of the components may be made without departing from the spirit or scope of the claims as set forth herein. Additional, different or fewer components may be provided and components may be combined. Alternatively or in addition, a component may be implemented by several components.

The above description illustrates the invention by way of example and not by way of limitation. This description clearly enables one skilled in the art to make and use the invention, and describes several embodiments, adaptations, variations, alternatives and uses of the invention, including what is presently believed to be the best mode of carrying out the invention. Additionally, it is to be understood that the invention is not limited in its application to the details of construction and the arrangement of components set forth in the following description or illustrated in the drawings. The invention is capable of other embodiments and of being practiced or carried out in various ways. Also, it will be understood that the phraseology and terminology used herein is for the purpose of description and should not be regarded as limiting.

Having described aspects of the invention in detail, it will be apparent that modifications and variations are possible without departing from the scope of aspects of the invention as defined in the appended claims. As various changes could be made in the above constructions, products, and methods without departing from the scope of aspects of the invention, it is intended that all matter contained in the above description and shown in the accompanying drawings shall be interpreted as illustrative and not in a limiting sense.

REFERENCES

1. Coley W B. The Treatment of Malignant Tumors by Repeated Inoculations of Erysipelas with a Report of Ten Original Cases. American Journal of Medical Sciences. 1893; 105:487-511.
2. Brody J D, Ai W Z, Czerwinski D K, Torchia J A, Levy M, Advani R H, et al. In situ vaccination with a TLR9 agonist induces systemic lymphoma regression: a phase I/II study. Journal of clinical oncology: official journal of the American Society of Clinical Oncology. 2010; 28(28): 4324-32. PMCID: 2954133.
3. Zappasodi R, Pupa S M, Ghedini G C, Bongarzone I, Magni M, Cabras A D, et al. Improved clinical outcome in indolent B-cell lymphoma patients vaccinated with autologous tumor cells experiencing immunogenic death. Cancer research. 2010; 70(22):9062-72.
4. Obeid M, Panaretakis T, Joza N, Tufi R, Tesniere A, van Endert P, et al. Calreticulin exposure is required for the immunogenicity of gamma-irradiation and UVC light-induced apoptosis. Cell death and differentiation. 2007; 14(10):1848-50.
5. Obeid M, Tesniere A, Ghiringhelli F, Fimia G M, Apetoh L, Perfettini J L, et al. Calreticulin exposure dictates the immunogenicity of cancer cell death. Nature medicine. 2007; 13(1):54-61.
6. Ma Y, Aymeric L, Locher C, Mattarollo S R, Delahaye N F, Pereira P, et al. Contribution of IL-17-producing {gamma}{delta} T cells to the efficacy of anticancer chemotherapy. The Journal of experimental medicine. 2011; 208(3):491-503. PMCID: 3058575.
7. Salem A K, Weiner G J. CpG oligonucleotides as immunotherapeutic adjuvants: innovative applications and delivery strategies. Advanced drug delivery reviews. 2009; 61(3):193-4.
8. Weiner G J. CpG oligodeoxynucleotide-based therapy of lymphoid malignancies. Advanced drug delivery reviews. 2009; 61(3):263-7.
9. Lu J M, Wang X, Marin-Muller C, Wang H, Lin P H, Yao Q, et al. Current advances in research and clinical applications of PLGA-based nanotechnology. Expert Rev Mol. Diagn. 2009; 9(4):325-41. PMCID: 2701163.
10. Zhang X Q, Dahle C E, Baman N K, Rich N, Weiner G J, Salem A K. Potent antigen-specific immune responses stimulated by codelivery of CpG ODN and antigens in degradable microparticles. J. Immunother. 2007; 30(5): 469-78.
11. Zhang X Q, Dahle C E, Weiner G J, Salem A K. A comparative study of the antigen-specific immune response induced by co-delivery of CpG ODN and antigen using fusion molecules or biodegradable microparticles. J Pharm Sci. 2007; 96(12):3283-92.
12. Weinberg B D, Ai H, Blanco E, Anderson J M, Gao J. Antitumor efficacy and local distribution of doxorubicin via intratumoral delivery from polymer millirods. J Biomed Mater Res A. 2007; 81(1):161-70.
13. Idani H, Matsuoka J, Yasuda T, Kobayashi K, Tanaka N. Intra-tumoral injection of doxorubicin (adriamycin) encapsulated in liposome inhibits tumor growth, prolongs survival time and is not associated with local or systemic side effects. International journal of cancer Journal international du cancer. 2000; 88(4):645-51.
14. Voulgaris S, Partheni M, Karamouzis M, Dimopoulos P, Papadakis N, Kalofonos H P. Intratumoral doxorubicin in patients with malignant brain gliomas. American journal of clinical oncology. 2002; 25(1):60-4.
15. Li J, Song W, Czerwinski D K, Varghese B, Uematsu S, Akira S, et al. Lymphoma immunotherapy with CpG oligodeoxynucleotides requires TLR9 either in the host or in the tumor itself. Journal of immunology. 2007; 179(4): 2493-500.
16. Hartmann G, Weiner G J, Krieg A M. CpG DNA: a potent signal for growth, activation, and maturation of human dendritic cells. Proceedings of the National Academy of Sciences of the United States of America. 1999; 96(16):9305-10.
17. Weiner G J, Liu H M, Wooldridge J E, Dahle C E, Krieg A M. Immunostimulatory Oligodeoxynucleotides Containing the CpG Motif are Effective As Immune Adjuvants In Tumor Antigen Immunization. Proceedings of the National Academy of Sciences of the United States of America. 1997; 94(20):10833-7.
18. Jahrsdorfer B, Hartmann G, Racila E, Jackson W, Muhlenhoff L, Meinhardt G, et al. CpG DNA increases primary malignant B cell expression of costimulatory molecules and target antigens. J Leukoc Biol. 2001; 69(1):81-8.
19. Jahrsdorfer B, Muhlenhoff L, Blackwell S E, Wagner M, Poeck H, Hartmann E, et al. B-cell lymphomas differ in their responsiveness to CpG oligodeoxynucleotides. Clin Cancer Res. 2005; 11(4):1490-9.
20. Link B K, Ballas Z K, Weisdorf D, Wooldridge J E, Bossier A D, Shannon M, et al. Oligodeoxynucleotide CpG 7909 delivered as intravenous infusion demonstrates immunologic modulation in patients with previously treated non-hodgkin lymphoma. J. Immunother. 2006; 29(5):558-68.
21. Leonard J P, Link B K, Emmanouilides C, Gregory S A, Weisdorf D, Andrey J, et al. Phase I Trial of Toll-Like Receptor 9 Agonist PF-3512676 with and Following Rituximab in Patients with Recurrent Indolent and Aggressive Non Hodgkin's Lymphoma. Clin Cancer Res. 2007; 13(20):6168-74.
22. Zent C S, Smith B J, Ballas Z K, Wooldridge J E, Link B K, Call T G, et al. A Phase I Clinical Trial of CpG Oligonucleotide 7909 (PF-03512676) in Patients with Previously Treated Chronic Lymphocytic Leukemia. Leukemia & lymphoma. 2011.
23. Heckelsmiller K, Rall K, Beck S, Schlamp A, Seiderer J, Jahrsdorfer B, et al. Peritumoral CpG DNA elicits a coordinated response of CD8 T cells and innate effectors to cure established tumors in a murine colon carcinoma model. J. Immunol. 2002; 169(7):3892-9.
24. Betting D J, Yamada R E, Kafi K, Said J, van Rooijen N, Timmerman J M. Intratumoral but not systemic delivery of CpG oligodeoxynucleotide augments the efficacy of anti-CD20 monoclonal antibody therapy against B cell lymphoma. Journal of immunotherapy. 2009; 32(6):622-31.
25. Molenkamp B G, van Leeuwen P A, Meijer S, Sluijter B J, Wijnands P G, Baars A, et al. Intradermal CpG-B activates both plasmacytoid and myeloid dendritic cells in the sentinel lymph node of melanoma patients. Clinical cancer research: an official journal of the American Association for Cancer Research. 2007; 13(10):2961-9.

26. Topalian S L, Weiner G, Pardoll D M. Cancer Immunotherapy Comes of Age. Journal of Clinical Oncology. In Press.
27. Zou W, Chen L. Inhibitory B7-family molecules in the tumour microenvironment. Nature reviews Immunology. 2008; 8(6):467-77.
28. Hodi F S, O'Day S J, McDermott D F, Weber R W, Sosman J A, Haanen J B, et al. Improved survival with ipilimumab in patients with metastatic melanoma. The New England journal of medicine. 2010; 363(8):711-23.
29. Keir M E, Butte M J, Freeman G J, Sharpe A H. PD-1 and its ligands in tolerance and immunity. Annu Rev Immunol. 2008; 26:677-704.
30. Yang Z Z, Novak A J, Ziesmer S C, Witzig T E, Ansell S M. Attenuation of CD8(+) T-cell function by CD4(+) CD25(+) regulatory T cells in B-cell non-Hodgkin's lymphoma. Cancer research. 2006; 66(20):10145-52. PMCID: 2680600.
31. Yang Z Z, Novak A J, Stenson M J, Witzig T E, Ansell S M. Intratumoral CD4+CD25+ regulatory T-cell-mediated suppression of infiltrating CD4+ T cells in B-cell non-Hodgkin lymphoma. Blood. 2006; 107(9):3639-46. PMCID: 1895773.
32. Wilcox R A, Feldman A L, Wada D A, Yang Z Z, Comfere N I, Dong H, et al. B7-H1 (PD-L1, CD274) suppresses host immunity in T-cell lymphoproliferative disorders. Blood. 2009; 114(10):2149-58. PMCID: 2744574.
33. Houot R, Levy R. T-cell modulation combined with intratumoral CpG cures lymphoma in a mouse model without the need for chemotherapy. Blood. 2009; 113(15):3546-52. PMCID: 2668854.
34. Weisman H F, Bartow T, Leppo M K, Marsh H C, Jr., Carson G R, Concino M F, et al. Soluble human complement receptor type 1: in vivo inhibitor of complement suppressing post-ischemic myocardial inflammation and necrosis. Science. 1990; 249(4965):146-51.

The invention claimed is:

1. A chemo-immunotherapeutic composition comprising: microparticles comprising a chemically modified surface having a net positive charge; a chemotherapeutic agent; and an immune adjuvant comprising an oligonucleotide, wherein the immune adjuvant is adsorbed on the chemically modified surface of the microparticles.

2. The composition of claim 1, wherein the microparticles comprise a polymeric material.

3. The composition of claim 2, wherein the polymeric material is PLGA.

4. The composition of claim 1, wherein the chemotherapeutic agent is doxorubicin, and the immune adjuvant is CpG.

5. The composition of claim 1, wherein the chemically modified surface of the microparticles comprises a polyamidoamine-modified surface.

* * * * *